United States Patent
Berry et al.

(10) Patent No.: US 8,546,563 B2
(45) Date of Patent: *Oct. 1, 2013

(54) COMPOUNDS WHICH MODULATE THE CB2 RECEPTOR

(75) Inventors: Angela Berry, Gaylordsville, CT (US); Doris Riether, Newtown, CT (US); Renee M. Zindell, New Milford, CT (US); Nigel James Blumire, Didcot (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 206 days.

This patent is subject to a terminal disclaimer.

(21) Appl. No.: 12/741,260

(22) PCT Filed: Oct. 30, 2008

(86) PCT No.: PCT/US2008/081680
§ 371 (c)(1),
(2), (4) Date: Jun. 17, 2010

(87) PCT Pub. No.: WO2009/061652
PCT Pub. Date: May 14, 2009

(65) Prior Publication Data
US 2010/0331304 A1 Dec. 30, 2010

Related U.S. Application Data

(60) Provisional application No. 60/986,004, filed on Nov. 7, 2007.

(51) Int. Cl.
| | |
|---|---|
| *C07D 205/00* | (2006.01) |
| *C07D 413/12* | (2006.01) |
| *C07D 213/00* | (2006.01) |
| *C07D 277/82* | (2006.01) |
| *C07D 231/10* | (2006.01) |
| *C07D 285/08* | (2006.01) |
| *C07D 261/14* | (2006.01) |
| *C07D 249/14* | (2006.01) |
| *A61K 31/535* | (2006.01) |
| *A61K 31/445* | (2006.01) |
| *A61K 31/425* | (2006.01) |
| *A61K 31/41* | (2006.01) |
| *A61K 31/42* | (2006.01) |
| *A61K 31/44* | (2006.01) |

(52) U.S. Cl.
USPC ........ 544/140; 546/269.1; 546/309; 548/163; 548/195; 548/371; 548/128; 548/950; 548/245; 548/265.4; 514/236.8; 514/326; 514/371; 514/367; 514/364; 514/315; 514/380; 514/352; 514/383; 514/372

(58) Field of Classification Search
None
See application file for complete search history.

(56) References Cited

U.S. PATENT DOCUMENTS

| | | | |
|---|---|---|---|
| 3,116,284 A | 12/1963 | Testa | |
| 3,117,128 A | 1/1964 | Mooradian | |
| 3,577,462 A | 5/1971 | Bruce et al. | |
| 3,966,809 A | 6/1976 | Baker et al. | |
| 4,257,954 A | 3/1981 | Schmidt et al. | |
| 4,535,087 A | 8/1985 | Spatz | |
| 4,672,065 A | 6/1987 | Spatz | |
| 4,734,125 A | 3/1988 | Gehring et al. | |
| 4,859,707 A | 8/1989 | Loftsson et al. | |
| 5,256,658 A | 10/1993 | Hsi et al. | |
| 5,428,037 A | 6/1995 | Pascal et al. | |
| 5,475,130 A | 12/1995 | Sato et al. | |
| 5,491,170 A * | 2/1996 | Lee et al. ............ 514/538 | |
| 5,571,921 A | 11/1996 | Bender et al. | |
| 5,583,147 A | 12/1996 | Ko et al. | |
| 5,656,634 A | 8/1997 | Chang et al. | |
| 5,847,153 A | 12/1998 | Warpehoski et al. | |
| 5,958,940 A | 9/1999 | Rane et al. | |
| 5,968,929 A | 10/1999 | Blythin et al. | |
| 6,057,371 A | 5/2000 | Glennon | |
| 6,176,442 B1 | 1/2001 | Eicher et al. | |
| 6,221,866 B1 | 4/2001 | Brendel et al. | |
| 6,355,653 B1 | 3/2002 | Trottmann et al. | |
| 6,359,009 B1 | 3/2002 | Diehl et al. | |

(Continued)

FOREIGN PATENT DOCUMENTS

| | | |
|---|---|---|
| CH | 312963 A | 3/1956 |
| DE | 1080563 B | 12/1957 |

(Continued)

OTHER PUBLICATIONS

Zindell, R. et al., "Discovery of a novel class of CB2 agonists". General Poster Session. The 235th ACS National Meeting, New Orleans, LA, USA. Apr. 6-10, 2008.
Office Action mailed Jan. 13, 2012 for U.S. Appl. No. 12/882,328, filed Sep. 15, 2010. Inventor: Alessandra Bartolozzi.
Abstract in English for JP2003155285, May 27, 2003, Inventor: T. Makoto.
Beilstein Database—Beilstein Registry No. 1084348. CAS Registry No. 6125-38-8. Beilstein Institute for Organic Chemistry. 1966, Abstract.

(Continued)

*Primary Examiner* — Nyeemah A Grazier
(74) *Attorney, Agent, or Firm* — Michael P. Morris; Anthony P. Bottino

(57) ABSTRACT

Compounds of formula (I) are disclosed. Compounds according to the invention bind to and are agonists of the CB2 receptor, and are useful for treating inflammation. Those compounds which are agonists are additionally useful for treating pain.

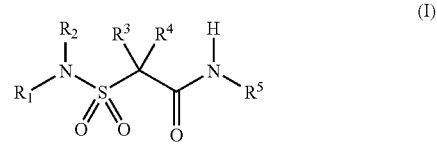

(I)

10 Claims, No Drawings

(56) References Cited

U.S. PATENT DOCUMENTS

| | | |
|---|---|---|
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 6,756,404 B2 * | 6/2004 | Livinghouse ............. 514/471 |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,776,897 B2 | 8/2010 | Murakami et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 8,299,103 B2 | 10/2012 | Bartolozzi et al. |
| 8,299,111 B2 | 10/2012 | Berry et al. |
| 8,329,735 B2 | 12/2012 | Erman et al. |
| 2002/0099035 A1 | 7/2002 | Sandanayaka et al. |
| 2004/0067999 A1 | 4/2004 | Block et al. |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2006/0061726 A1 | 3/2006 | Okuyama |
| 2006/0079557 A1 | 4/2006 | Dolle et al. |
| 2007/0021403 A1 | 1/2007 | Abouabdellah et al. |
| 2007/0021430 A1 | 1/2007 | Chen et al. |
| 2007/0093501 A1 | 4/2007 | Kubo et al. |
| 2007/0179126 A1 | 8/2007 | Casellas et al. |
| 2007/0191340 A1 | 8/2007 | Zindell et al. |
| 2007/0213311 A1 | 9/2007 | Li et al. |
| 2008/0039464 A1 | 2/2008 | Berry et al. |
| 2008/0064690 A1 | 3/2008 | Atkinson et al. |
| 2008/0081342 A1 | 4/2008 | Fung |
| 2008/0081822 A1 | 4/2008 | Berry et al. |
| 2009/0163545 A1 | 6/2009 | Goldfarb |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |

FOREIGN PATENT DOCUMENTS

| | | |
|---|---|---|
| EP | 0628555 | 12/1994 |
| EP | 0929519 | 7/1999 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |
| GB | 884258 A | 12/1961 |
| GB | 1237126 A | 6/1971 |
| JP | 61017955 | 2/1986 |
| JP | 61027905 U | 2/1986 |
| JP | 61126071 A | 6/1986 |
| JP | 2003155285 | 5/2003 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9811097 A1 | 3/1998 |
| WO | 9813340 | 4/1998 |
| WO | 9838163 A1 | 9/1998 |
| WO | WO 9965889 A1 * | 12/1999 |
| WO | 0008015 A2 | 2/2000 |
| WO | 0100573 | 1/2001 |
| WO | 0129007 | 4/2001 |
| WO | 0164651 | 9/2001 |
| WO | 02051806 | 7/2002 |
| WO | 02088089 A1 | 7/2002 |
| WO | 02062750 | 8/2002 |
| WO | 03037274 A2 | 5/2003 |
| WO | 03055482 | 7/2003 |
| WO | 03000807 | 12/2003 |
| WO | 2004000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004026301 A1 | 4/2004 |
| WO | 2004029027 | 4/2004 |
| WO | 2004042351 A2 | 5/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006030805 A1 | 3/2006 |
| WO | 2006060461 | 6/2006 |
| WO | 2006074445 A2 | 7/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 | 6/2007 |
| WO | 2007070760 A2 | 6/2007 |
| WO | 2007080382 A1 | 7/2007 |
| WO | 2007102059 | 9/2007 |
| WO | 2007118041 | 10/2007 |
| WO | 2007140385 A2 | 12/2007 |
| WO | 2008014199 A | 1/2008 |
| WO | 2008023159 A1 | 2/2008 |
| WO | 2008039645 A | 4/2008 |
| WO | 2008048914 A1 | 4/2008 |
| WO | 2008064054 | 5/2008 |
| WO | 2008098025 A1 | 8/2008 |
| WO | 2008104994 A2 | 9/2008 |
| WO | 2009055357 A1 | 4/2009 |
| WO | 2009061652 A1 | 5/2009 |
| WO | 2009077533 | 6/2009 |
| WO | 2009105509 A1 | 8/2009 |
| WO | 2009140089 A2 | 11/2009 |
| WO | 2010005782 A1 | 1/2010 |
| WO | 2010036630 A2 | 4/2010 |
| WO | 2010036631 A2 | 4/2010 |
| WO | 2010077836 A2 | 7/2010 |
| WO | 2010096371 A2 | 8/2010 |
| WO | 2010147791 A1 | 12/2010 |
| WO | 2010147792 A2 | 12/2010 |
| WO | 2011037795 | 3/2011 |
| WO | 2011088015 A1 | 7/2011 |
| WO | 2011109324 A1 | 9/2011 |
| WO | 2012012307 A1 | 1/2012 |

OTHER PUBLICATIONS

Beilstein Database—Beilstein Registry No. 1179643. CAS Registry No. 54890-73-2. Beilstein Institute for Organic Chemistry. 1974, Abstract.
Beilstein Database—Beilstein Registry No. 5396840. CAS Registry No. 54890-82-3. Beilstein Institute for Organic Chemistry. 1974, Abstract.
Beilstein Database—Beilstein Registry No. 5398283. CAS Registry No. 68558-02-01. Beilstein Institute for Organic Chemistry. 1978, Abstract.
Beilstein Database—Beilstein Registry No. 857451. CAS Registry No. 37901-58-9. Beilstein Institute for Organic Chemistry. 1972, Abstract.
Carenzi, A, et al., "New Isoxazole Derivatives Provided with Antihypertensive Activity". Arzneimittel-Forschung, vol. 39, No. 6, 1989, p. 624-646.
Chem Abstract—Accession No. 126:89390, Abstract of JP8311026, Kumaiai Chemical Industry Co., Nov. 26, 1996.
ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.
Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60.
International Search Report for PCT/US2008/081680 mailed Feb. 17, 2009.
Kano, S. et al., "Formation of Some Heterocycles through Ring Transformation of 1-Arylaxetidin-2-Ones." Heterocycles, vol. 8, No. 1, Dec. 30, 1977, p. 411-416.
U.s. Appl. No. 13/022,866, filed Feb. 8, 2011, Inventor: Angela Berry.
U.S. Appl. No. 13/037,422, filed Mar. 1, 2011, Inventor: Monika Ermann.
Sheehan, J.C. et al, The Synthesis and Reactions of Some Substituted Beta-Lactams, 1951, Journal of the American Chemical Society, 73, 1761-1765.
Abstract in English for JP 61-027905, Feb. 7, 1986, and WO199626925, Sep. 1996, Derwent Abstract.
Abstract in English for JP 61-027955, Feb. 7, 1986, Derwent.
Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.
Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.
Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.
Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.
Arevalo-Martin, A. et al., "Therapeutic Action of Cannabinoids in a Murine model of Multiple Sclerosis", J. of Neuroscience, 2003, vol. 23, No. 7, p. 2511.
Atwell, G. J. et al., "Relationships between Structure and Kinetics of Cyclization of 2-Aminoaryl Amides: Potential Prodrugs of Cyclization-Activitated Aromatic Mustards"., XP-002465787, J. Med. Chem, 1994, 37, 371-380.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, (2004).
Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.
Baker, D. et al., "Cannabinoids control spasticity and tremor in a multiple sclerosis model", Nature, 2000, vol. 404, p. 84.

Baltzly, R. et al., "The preparation of N-mono-substituted and unsymmetrically disubstituted piperzines". Journal of American Chemical Society, vol. 66, 1944, pp. 263-265.
Baltzly,R. et al., "Unsymmetrically substituted piperazines. V. Piperazine ureas". The Journal of the American Chemical Society, vol. 76, 1954, pp. 1165-1166.
Balzarini, J. et al., "Antiretroviral activity of semisynthetic derivatives of glycopeptide antibiotics". J. Med. Chem., 2003, vol. 46, No. 13, pp. 2755-2764.
Binisti, C. et al., "Structure-Activity relationships in platelet-activating factor (PAF). 11—From PAF-antagonism to phospholipase A2 inhibition: syntheses and structure-activity relationships in 1-arylsulfamido-2-alkylpiperazines", Eur. J. Med. Chem., 2001, vol. 36, p. 809.
Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
Buckley, N. E. et al., "Immunomodulation by cannabinoids is absent in mice deficient for the cannabinoid CB2 receptor", Eur. J. Pharmacology, 2000, vol. 396, p. 141.
Caplus—1990:497413, Zara-Kaczian, Acta Chimica Hungarica.
Caplus—RN 112298-90-5 (Tommasi), retrieved from CAPLUS on Jan. 2, 2009.
Caplus—RN 262371-16-4 (Organ), retrieved from CAPLUS on Jan. 2, 2009.
Caplus—RN 57992-82-2 (Babayan), retrieved from CAPLUS on Jan. 2, 2009.
Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.
Chang, M. Y. et al, "Reaction of different a-sulfonyl acetamides with methyl acrylate". Tetrahedron 58 (2002) p. 5075-5080.
ChemAbstract: 246020-62-2 registry copyright ACS on STN, entered 1999. CHEMCATS.
ChemAbstracts: 693218-49-4 and 402562-90-7, (2004) and (2002), respectively.
Chen, D. et al., "Preparation, properties, and synthetic potentials of novel boronates in a flourous version (flourous boronates)". Organic Letters, vol. 4. No. 6, 2002, pp. 1003-1005.
Clark, N. G. et al., "The Fungicidal Activity of Substituted Acetanilides and Related Compounds". Biochemical Journal, 1953, vol. 55, p. 839-851.
Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.
Dav, Jr., R. A. et al., "Polarography of phenyl 2-thienyl and 2,2'-dithienyl ketones". 1953.
El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.
EP Office Action for Case 09-0388 dated Mar. 22, 2010.
Ermann, M. et al., "Arylsulfonamide CB2 receptor agonists: SAR and optimization of CB2 selectivity", Bioorganic and Medicinal Chemistry Letters 18 (2008) 1725-1729.
Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.
Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.
Evans, W. J. et al., "A Rearrangement of Carbamyl-sulphones and -sulphides". Journal of the Chemical Society, 1936, p. 329-331.
Faucher, A. M. et al., "Discovery of Small-Molecule Inhibitors of the ATPase Activity of Human Papillomavirus E1 Helicase", J. Med. Chem., 2004, vol. 47, p. 18.

Field, L. et al., "Grignard Reagents of Sulfones. IV. Reactions with Nitriles, Esters and an Isocyanate". Journal of American Society, vol. 78, 1956, p. 4389-4394.

Field, L., et al., "Methyl p-Tolyl Sulfone", Organic Syntheses, Coll. vol. 4, p. 674, 1963; vol. 38, p. 62, (1958).

Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.

Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.

Gartst, M., et al., "Hydroformylation of bisolefinic amine derivatives catalyzed by cobalt and rhodium". Journal of Organic Chemistry, vol. 46, 1981, pp. 4433-4438.

Gavalda, et al N-Sulfonyl hydroxamate derivataties as inhibitors of class II fructose-1, 6-diphosphate aldolase, Bioorganic & Medicinal Chemistry Letter, 2005, vol. 15, No. 24, pp. 5375-5377.

Goldschmidt,ST. et al., "Biphenyl derivatives II. Basic 4-Biphenyl Compounds". Receuil Travaux Chimiques Des Pays-Bas, vol. 69, 1950, pp. 1109-1117.

Grothe, V. W. et al. "Effect of Potassium Sulfhydrate etc. on Chloroacetylanilides". Archiv der Pharmazie (Weinheim), vol. 238, 1980, p. 600-614.

Hanus, L. et al., "HU-308: A specific agonist for CB2, a peripheral cannabinoid receptor", PNAS, 1999, vol. 96, No. 25, p. 14228.

Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.

Huang, X. et al., "A Novel Synthesis of Sulfones via the O.O-Diethylphosphorotellurite Ion-assisted Coupling of Arenesulfonyl Chlorides with Active Halides". Synthetic Communications, 20(15), 2291-2291-2295 (1990).

Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.

Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.

Iddon, B. et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.

Igarashi, J. et al., "Improved synthesis of quinine alkaloids with the Teoc protective group". Tetrahedron letters, Elsevier, Amsterdam, vol. 46, No. 37, 2005, pp. 6381-6384.

International Search Report for PCT/US2007/078341 mailed Jan. 31, 2008.

Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).

Johansen et al., AMPA Receptor Agonists: Resolution, Configurational Assignment, and Pharmacology of (+)-(S)- and (−)-(R)-2-Amino-3-(3-Hydroxy-5-(2-Pyridyl) Isoxazol-4-yl)Propionic Acid (1-Py-AMPA); Chirality, NewYork, 1997, vol. 9, No. 3, pp. 274-280.

Katoh, A., et al., "Synthesis of 6-(Bromoacetyl)Amino-2,3-Dimorpholino-Quinoxaline and Application to a new Fluorescence Derivatization Reagent of Fatty Acids fo the High-Performance Liquid Chromatographic Analysis", Heterocycles, 199, vol. 50, No. 1, p. 299.

Katz, L., et al., "Hydrazine Derivatives. II. Ortho-Mercapto-Pyridinecarbohydrazides", Contribution from Schenley Laboratories, Inc., 1953, p. 711.

Klein, T. W., et al., "The Cannabinoid system and immune modulation", J. Leukocyte Biology, 2003, vol. 74, p. 486.

Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.

Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.

Lambeng, N. et al., "Discovery of a Novel Piperidinyl-Sulfonyl Benzoic Ester, Active as CB1 Agonist" Poster. 231st ACS National Meeting, Atlanta, GA. Mar. 26-30, 2006.

Lesser, R. et al. "Homo-?-oxythionaphthene (4-Ketoisothiochromane". Charlottenburg, Industrial Chemistry Laboratory of the Institute of Technology, 1923, pp. 1642-1648.

Lutz, R. E. et al., "Antimalarials. Some piperazine derivatives". Journal of Organic Chemistry, vol. 12, 1947, pp. 771-775.

Mahmoud, A. M. et al., "Synthesis and Biological Activity of Some new 2-(N-Substituted Carboxamidomethyl Thio)-Naphth[1,2-d]Oxazoles—Part V". XP002068972, J. Indian Chem. Soc., vol. LIX, May 1982, pp. 675-677.

Malan Jr., T. P., et al., "CB2 cannabinoid receptor-mediated peripheral antinociception", Pain, 2001, vol. 93, p. 239.

Markley, L. D., et al., "Antipicomavirus activity of substituted Phenoxybenzenes and Phenoxypyridines", J. Med. Chem., 1986, vol. 29, p. 427.

Marx, I. E. et al., "Discovery of a-amidosulfones as potent and selective agonists of CB2: Synthesis, SAR, and pharmacokinetic properties". Bioorganic and Medicinal chemistry Letters, 2008. In press, accepted manuscript.

Messinger, P., "Sulfones via Mannich bases" Archiv der Pharmazie, 1973, vol. 306, No. 8, pp. 603-610, ISSN: 0365-6233. p. 607, compounds 28A-29C.

Miroshnikova, O.V. et al., "Structure-activity relationships in the series of eremomycin carboxamides". Journal of Antibiotics, vol. 53, No. 3, 2000, pp. 286-293.

Miyano, S, et al., "Kinetic Resolution of Racemic b-Hydroxy Amines by Enantioselective N-Oxide formation". Journal of Organic Chemistry, 1985, vol. 50, pp. 4350-4360.

Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.

Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.

Office Action from the EPO for 09-0388 dated Mar. 22, 2010.

Pollard, C. B. et al., "Some amides of piperazines". Journal of American Chemical Society, vol. 75, 1953, p. 491.

Revesz, L. et al., "Novel CCR1 antagonists with oral activity in the mouse collagen induced arthritis". Bioorganic and Medicinal Chemistry Letters, vol. 15, 2005, pp. 5160-5164.

Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.

Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.

Seidel M. C. et al., "Reaction of Substituted 2-carbethoxyacetyl-aminopyridines and similar compounds with triethyl orthoformate and zinc chloride". Rohm and Haas Company, Spring House, Pennsylvania 19477, 1989.

Sharkey, K. A. et al., "CB2 cannabinoid receptors: new vistas", The first International Conference devoted to studies of the CB2 cannabinoid receptor. Banff, Alberta, Canada, May 31-Jun. 3, 2007.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Smith, S. R., et al., "The anti-inflammatory activities of cannabinoid receptor ligands in mouse peritonitis models", Eur. J. Pharmacology, 2001, vol. 432, p. 107.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Swanson, D. M. et al., "Identification and biological evaluation of 4-*(3-trifluoremethylpyridin-2-yl)piperzine-1-carboxylic acid (5-trifluoremethylpyridin-2-yl)amide, a high affinity TRPV1 (VR1) vanilloid receptor antagonist". Journal Med. Chem, 2005, 48, pp. 1857-1872.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol, 82, 1999, pp. 354.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Ueber sulfonirte buttersauren", J. Prakt. Chem., 1899, 1991, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Venkov, A.P. et al., "A new synthesis of 1,2,3,40tetrahydro-2-methyl-4-phenylisoquinolines". Dept of Chemistry, University of Plovdiv, Bulgaria, pp. 253-255, (1990).

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al., "An enantioselective synthesis of sulphonamide hydroxamic acids as matrix metalloproteinase inhibitors", Pergamon, Tetrahedron Letters 43 (2002) 683-685.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho-lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

* cited by examiner

COMPOUNDS WHICH MODULATE THE CB2 RECEPTOR

APPLICATION DATA

This application claims benefit to U.S. provisional application Ser. No. 60/986,004 filed Nov. 7, 2007.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system.

CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In its broadest generic aspect the invention provides compounds of the formula

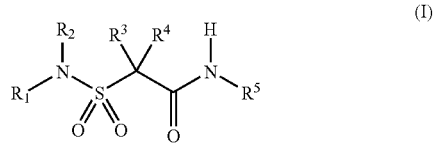

wherein:

R$^1$ is C$_{1-10}$ alkyl, C$_{3-10}$ cycloalkyl-C$_{0-2}$ alkyl- or heterocycle-C$_{0-2}$ alkyl- wherein the heterocycle is chosen from tetrahydropyranyl, tetrahydrofuranyl, dioxanyl, thiomorpholinyl, 1,1-dioxo-1λ$^6$-thiomorpholinyl, morpholinyl, piperidinyl, pyrrolidinyl, tetrahydrothienyl, sulfonalyl, tetrahydrothiopyranyl, 1,1-dioxo-tetrahydrothiopyranyl, imidazolidinyl, pyrazolidinyl, oxetanyl, each R$^1$ is optionally substituted with 1 to 3 substituents chosen from halogen, C$_{1-5}$ alkyl, C$_{3-10}$ cycloalkyl, hydroxy and C$_{1-6}$ alkoxy;

R$^2$ is hydrogen or C$_{1-5}$ alkyl;

or R$^1$ and R$^2$ together with the N atom to which they are attached form a 3- to 6-membered heterocyclic ring optionally substituted with 1-3 substituents chosen from C$_{1-10}$ alkyl, C$_{1-10}$ alkoxy, C$_{3-10}$ cycloalkyl, hydroxyl, C$_{1-3}$ alkylaminocarbonyl, C$_{1-3}$ dialkylaminocarbonyl, C$_{1-3}$ alkylcarbonyl, C$_{1-3}$ alkyl sulfonyl and halogen;

R$^3$ is methyl, ethyl, or isopropyl;

R$^4$ is H or methyl;

or

R$^3$ and R$^4$ together with the carbon they are attached to form a 3-4 membered cycloalkyl ring;

R$^5$ is C$_{1-10}$ alkyl optionally substituted by aryl or heteroaryl, or

R$^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, oxadiazolyl, pyrazolyl, triazolyl, pyridinyl or benzothiazolyl each optionally independently substituted with 1 to 3 substituents chosen from C$_{1-6}$ alkyl, C$_{1-5}$ alkoxycarbonyl, cyano, halogen, carbocycle and heteroaryl, each R$^5$ or it's substituents where possible are optionally partially or fully halogenated;

or a pharmaceutically acceptable salt thereof;

with the proviso that if R$^2$ is hydrogen then R$^1$ cannot be aryl.

In a first subgeneric aspect, the invention provides compounds of the formula I wherein, R$^1$ is C$_{1-10}$ alkyl, C$_{3-10}$ cycloalkyl-C$_{0-2}$ alkyl- or heterocycle-C$_{0-2}$ alkyl- wherein the heterocycle is chosen from tetrahydropyranyl, tetrahydrofuranyl, dioxanyl, thiomorpholinyl, 1,1-dioxo-1λ$^6$-thiomorpholinyl, morpholinyl, piperidinyl, pyrrolidinyl, tetrahydrothienyl, sulfonalyl, tetrahydrothiopyranyl, 1,1-dioxo-tetrahydrothiopyranyl, imidazolidinyl, pyrazolidinyl, oxetanyl, each R$^1$ is optionally substituted with 1 to 3 substituents chosen from halogen, C$_{1-5}$ alkyl, C$_{3-10}$ cycloalkyl, hydroxy and C$_{1-6}$ alkoxy;

R$^2$ is hydrogen or C$_{1-5}$ alkyl;

or R$^1$ and R$^2$ together with the N atom to which they are attached form a 3- to 6-membered heterocyclic ring optionally substituted with 1-3 substituents chosen from C$_{1-10}$ alkyl, C$_{1-10}$ alkoxy, C$_{3-10}$ cycloalkyl, hydroxyl, C$_{1-3}$ alkylaminocarbonyl, C$_{1-3}$ dialkylaminocarbonyl, C$_{1-3}$ alkylcarbonyl, C$_{1-3}$ alkyl sulfonyl and halogen;

R$^3$ is methyl, ethyl, or isopropyl;

R$^4$ is H or methyl;

or

R$^3$ and R$^4$ together with the carbon they are attached to form a 3-4 membered cycloalkyl ring;

R$^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, oxadiazolyl, pyrazolyl, triazolyl, pyridinyl or benzothiazolyl each optionally independently substituted with 1 to 3 substituents chosen from C$_{1-6}$ alkyl, C$_{1-5}$ alkoxycarbonyl, cyano, halogen, carbocycle and heteroaryl, each R$^5$ or it's substituents where possible are optionally partially or fully halogenated.

In a further subgeneric aspect, the invention provides compounds of the formula I wherein, R$^1$ is C$_{1-5}$ alkyl, C$_{3-6}$ cycloalkyl-C$_{0-2}$ alkyl- or heterocycle-C$_{0-2}$ alkyl- wherein the heterocycle is chosen from tetrahydropyranyl, tetrahydrofuranyl, dioxanyl, thiomorpholinyl, 1,1-dioxo-1λ$^6$-thiomorpholinyl, piperidinyl, pyrrolidinyl, tetrahydrothienyl, sulfonalyl, tetrahydrothiopyranyl, 1,1-dioxo-tetrahydrothiopyranyl, imidazolidinyl, pyrazolidinyl, oxetanyl, and morpholinyl, each R$^1$ is optionally independently substituted with 1 to 3 substituents chosen from halogen, C$_{1-5}$ alkyl, C$_{3-6}$ cycloalkyl, hydroxy and C$_{1-6}$ alkoxy;

R$^1$ and R$^2$ together with the N atom to which they are attached form morpholinyl, piperidinyl, azetidinyl or pyrrolidinyl homopiperidinyl, thiomorpholinyl, 1,1-dioxo-1λ$^6$-thiomorpholinyl, piperazinyl, each optionally substituted with 1-3 substituents chosen from C$_{1-3}$ alkyl, C$_{1-3}$ alkoxy, C$_{3-6}$ cycloalkyl, C$_{1-3}$ alkylaminocarbonyl, C$_{1-3}$ dialkylaminocarbonyl, C$_{1-3}$ alkylcarbonyl, C$_{1-3}$ alkyl sulfonyl and halogen;

R$^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, pyrazolyl, triazolyl, pyridinyl or benzothiazolyl each R$^5$ substituent is further optionally substituted with 1 to 3 substituents chosen from C$_{1-5}$ alkyl, C$_{1-5}$ alkoxycarbonyl, cyano, halogen, phenyl, C$_{3-10}$ cycloalkyl, furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, pyrazolyl, triazolyl, pyridinyl, and benzothiazolyl, each R$^5$ or it's substituents where possible are optionally partially or fully halogenated.

In a further subgeneric aspect, the invention provides compounds of the formula I wherein, R$^1$ is C$_{1-5}$ alkyl, C$_{3-6}$ cycloalkyl, C$_{3-6}$ cycloalkylmethyl, tetrahydropyranyl, tetrahydrofuranyl or morpholinyl, each optionally independently substituted with 1 to 3 substituents chosen from halogen, C$_{1-3}$ alkyl, C$_{3-6}$ cycloalkyl and C$_{1-3}$ alkoxy;

R$^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, pyrazolyl, triazolyl, pyridinyl or benzothiazolyl each R$^5$ substituent is further optionally substituted with 1 to 3 substituents chosen from C$_{1-5}$ alkyl, C$_{1-5}$ alkoxycarbonyl, cyano, halogen, phenyl, C$_{3-6}$ cycloalkyl and pyridinyl, each R$^5$ or it's substituents where possible are optionally partially or fully halogenated.

In a further subgeneric aspect, the invention provides compounds of the formula I wherein, R$^1$ is C$_{1-5}$ alkyl, C$_{3-6}$ cycloalkyl, cyclohexylmethyl or tetrahydropyranyl, each optionally independently substituted with 1 to 3 substituents chosen from halogen, C$_{1-3}$ alkyl, C$_{3-6}$ cycloalkyl and C$_{1-4}$ alkoxy;

R$^1$ and R$^2$ together with the N atom to which they are attached form morpholinyl, piperidinyl, azetidinyl or pyrrolidinyl each optionally substituted with 1-3 substituents chosen from C$_{1-3}$ alkyl, C$_{1-3}$ alkoxy, C$_{3-6}$ cycloalkyl, C$_{1-3}$ alkylaminocarbonyl, C$_{1-3}$ dialkylaminocarbonyl, C$_{1-3}$ alkylcarbonyl, C$_{1-3}$ alkyl sulfonyl and halogen In a further subgeneric aspect, the invention provides compounds of the formula I wherein, $R^1$ is $C_{1-5}$ alkyl, $C_{3-6}$ cycloalkyl or tetrahydropyranyl, each optionally independently substituted with 1 to 3 substituents chosen from halogen, $C_{1-3}$ alkyl, $C_{1-3}$ alkoxy and $C_{3-6}$ cycloalkyl.

In another subgeneric aspect, the invention provides compounds of the formula I:

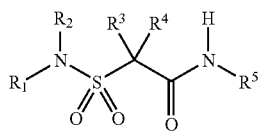

wherein for the formula (I)

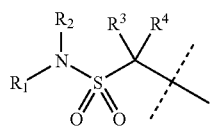

is chosen members of column A in Table I, and

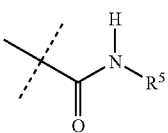

is chosen members of column B in Table I:

TABLE I-continued
| A | B |
|---|---|
| 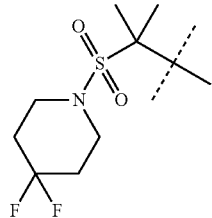 | 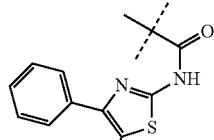 |
| 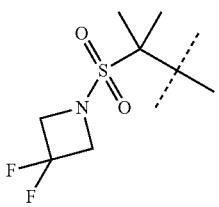 | 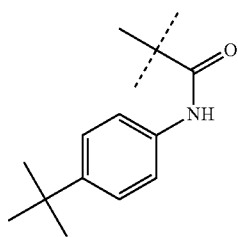 |
| 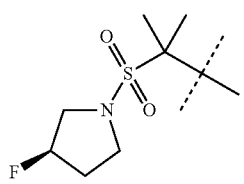 | 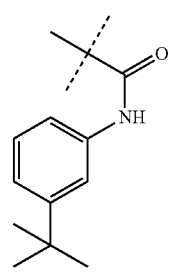 |
| 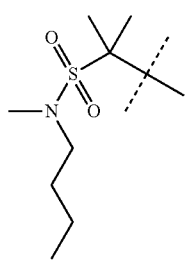 | 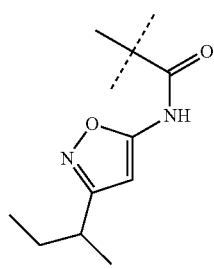 |
|  | 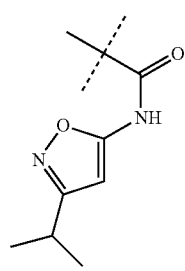 |
|  | 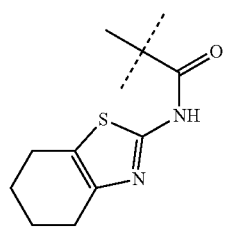 |
TABLE I-continued
| A | B |
|---|---|
|  | 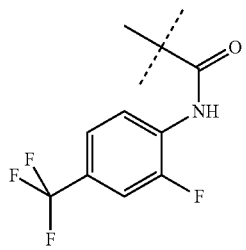 |
|  | 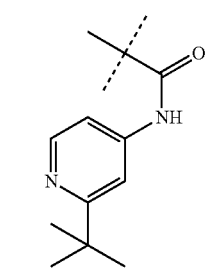 |
|  | 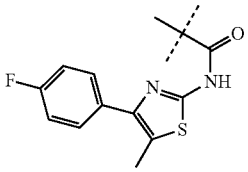 |
|  | 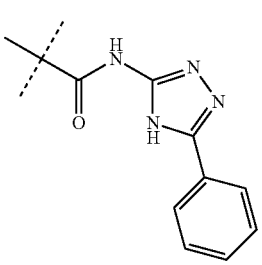 |
|  | 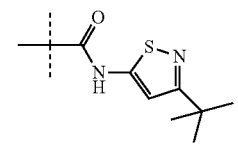 |

TABLE I-continued

| A | B |
|---|---|
| | 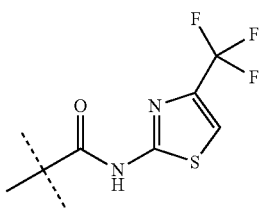 |
| | 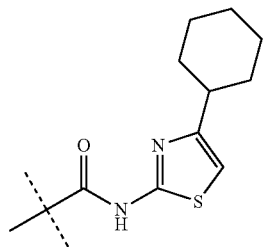 | or a pharmaceutically acceptable salt thereof.

In another embodiment, the invention provides compounds in Table II which can be made in view of the general schemes, examples and methods known in the art.

TABLE II

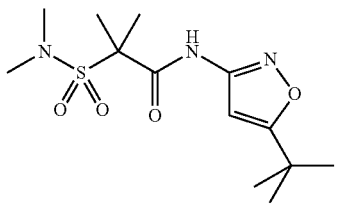 [SMILES: CN(C)S(=O)(=O)C(C)(C)C(=O)Nc1cc(C(C)(C)C)on1]

N-(5-tert-Butyl-isoxazol-3-yl)-2-dimethylsulfamoyl-2-methyl-propionamide

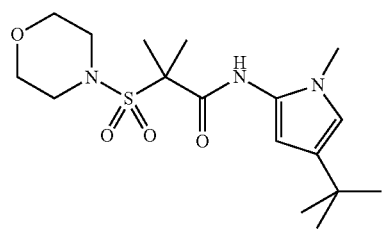 [SMILES: Cn1cc(C(C)(C)C)cc1NC(=O)C(C)(C)S(=O)(=O)N1CCOCC1]

N-(5-tert-Butyl-2-methyl-2H-pyrazol-3-yl)-2-methyl-2-(morpholine-4-sulfonyl)-propionamide

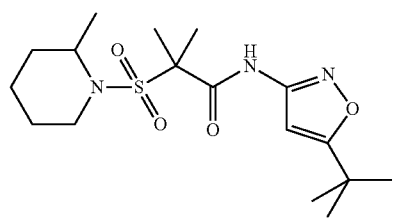 [SMILES: CC1CCCCN1S(=O)(=O)C(C)(C)C(=O)Nc1cc(C(C)(C)C)on1]

N-(5-tert-Butyl-isoxazol-3-yl)-2-methyl-2-(2-methyl-piperidine-1-sulfonyl)-propionamide

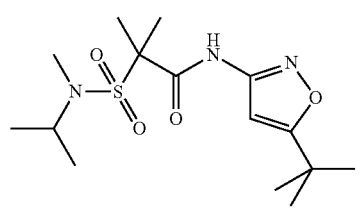 [SMILES: CC(C)N(C)S(=O)(=O)C(C)(C)C(=O)Nc1cc(C(C)(C)C)on1]

N-(5-tert-Butyl-isoxazol-3-yl)-2-(isopropyl-methyl-sulfamoyl)-2-methyl-propionamide TABLE II-continued 2-(Azetidine-1-sulfonyl)-N-(5-tert-butyl-isoxazol-3-yl)-2-methyl-propionamide N-(5-tert-Butyl-isoxazol-3-yl)-2-methyl-2-(pyrrolidine-1-sulfonyl)-propionamide N-(5-tert-Butyl-isoxazol-3-yl)-2-cyclopropylsulfamoyl-2-methyl-propionamide N-(5-tert-Butyl-isoxazol-3-yl)-2-cyclohexylsulfamoyl-2-methyl-propionamide N-(5-tert-Butyl-isoxazol-3-yl)-2-methyl-2-(piperidine-1-sulfonyl)-propionamide N-(5-tert-Butyl-isoxazol-3-yl)-2-cyclopentylsulfamoyl-2-methyl-propionamide N-(5-tert-Butyl-isoxazol-3-yl)-2-(4-methoxy-piperidine-1-sulfonyl)-2-methyl-propionamide TABLE II-continued

| Structure | Name |
|---|---|
| 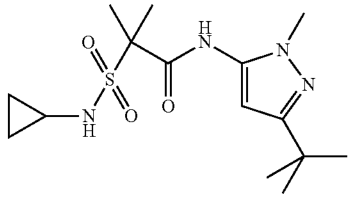 [SMILES: Cn1nc(C(C)(C)C)cc1NC(=O)C(C)(C)S(=O)(=O)NC1CC1] | N-(5-tert-Butyl-2-methyl-2H-pyrazol-3-yl)-2-cyclopropylsulfamoyl-2-methyl-propionamide |
| 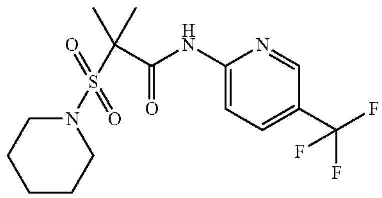 [SMILES: CC(C)(C(=O)Nc1ccc(C(F)(F)F)cn1)S(=O)(=O)N1CCCCC1] | 2-Methyl-2-(piperidine-1-sulfonyl)-N-(5-trifluoromethyl-pyridin-2-yl)-propionamide |
| 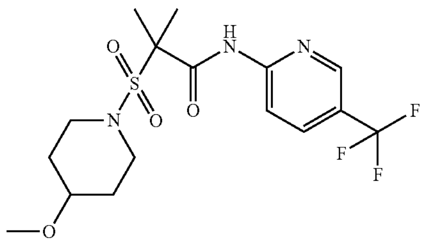 [SMILES: COC1CCN(S(=O)(=O)C(C)(C)C(=O)Nc2ccc(C(F)(F)F)cn2)CC1] | 2-(4-Methoxpiperidine-1-sulfonyl)2-methyl-N-(5-trifluoromethyl-pyridin-2-yl)-propionamide |
| 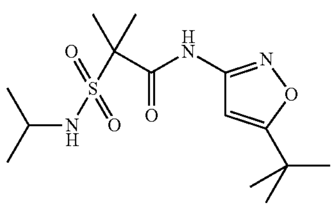 [SMILES: CC(C)NS(=O)(=O)C(C)(C)C(=O)Nc1cc(C(C)(C)C)on1] | N-(5-tert-Butyl-isoxazol-3-yl)-2-isopropylsulfamoyl-2-methyl-propionamide |
| 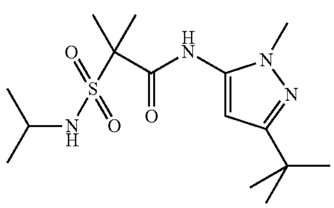 [SMILES: CC(C)NS(=O)(=O)C(C)(C)C(=O)Nc1cc(C(C)(C)C)nn1C] | N-(5-tert-Butyl-2-methyl-2H-pyrazol-3-yl)-2-isopropylsulfamoyl-2-methyl-propionamide |
| 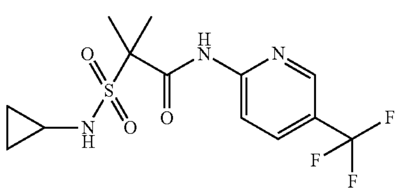 [SMILES: CC(C)(C(=O)Nc1ccc(C(F)(F)F)cn1)S(=O)(=O)NC1CC1] | 2-Cyclopropylsulfamoyl-2-methyl-N-(5-trifluoromethyl-pyridin-2-yl)-propionamide |
| 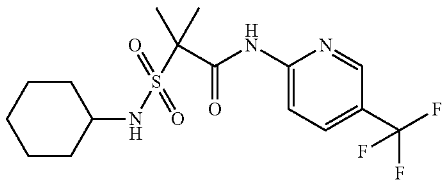 [SMILES: CC(C)(C(=O)Nc1ccc(C(F)(F)F)cn1)S(=O)(=O)NC1CCCCC1] | 2-Cyclohexylsulfamoyl-2-methyl-N-(5-trifluoromethyl-pyridin-2-yl)-propionamide |
| 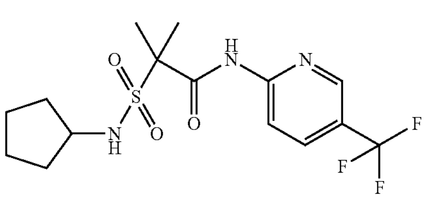 [SMILES: CC(C)(C(=O)Nc1ccc(C(F)(F)F)cn1)S(=O)(=O)NC1CCCC1] | 2-Cyclopentylsulfamoyl-2-methyl-N-(5-trifluoromethyl-pyridin-2-yl)-propionamide |

TABLE II-continued

| Structure | Name |
|---|---|
| 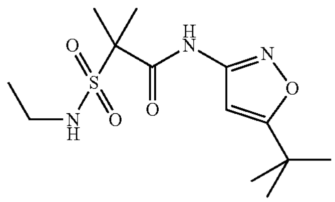 [SMILES: CCNS(=O)(=O)C(C)(C)C(=O)Nc1cc(C(C)(C)C)on1] | N-(5-tert-Butyl-isoxazol-3-yl)-2-ethylsulfamoyl-2-methyl-propionamide |
| 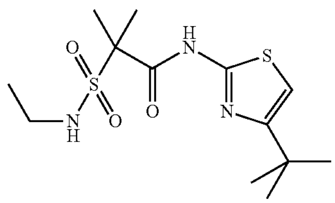 [SMILES: CCNS(=O)(=O)C(C)(C)C(=O)Nc1nc(C(C)(C)C)cs1] | N-(4-tert-Butyl-thiazol-2-yl)-2-ethylsulfamoyl-2-methyl-propionamide |
| 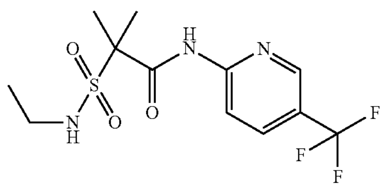 [SMILES: CCNS(=O)(=O)C(C)(C)C(=O)Nc1ccc(C(F)(F)F)cn1] | 2-Ethylsulfamoyl-2-methyl-N-(5-trifluoromethyl-pyridin-2-yl)-propionamide |
| 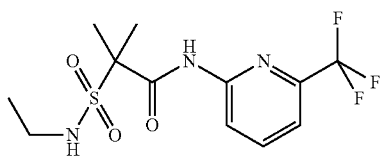 [SMILES: CCNS(=O)(=O)C(C)(C)C(=O)Nc1cccc(C(F)(F)F)n1] | 2-Ethylsulfamoyl-2-methyl-N-(6-trifluoromethyl-pyridin-2-yl)-propionamide |
| 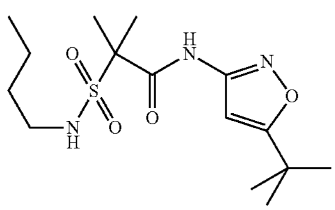 [SMILES: CCCCNS(=O)(=O)C(C)(C)C(=O)Nc1cc(C(C)(C)C)on1] | N-(5-tert-Butyl-isoxazol-3-yl)-2-butylsulfamoyl-2-methyl-propionamide |
| 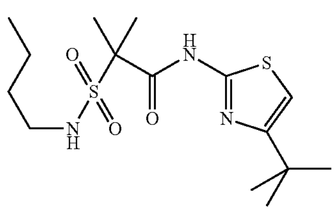 [SMILES: CCCCNS(=O)(=O)C(C)(C)C(=O)Nc1nc(C(C)(C)C)cs1] | 2-Butylsulfamoyl-N-(4-tert-butyl-thiazol-2-yl)-2-methyl-propionamide |
| 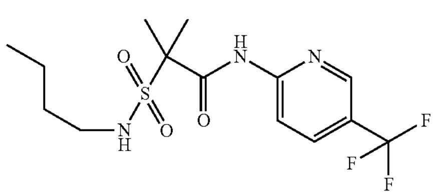 [SMILES: CCCCNS(=O)(=O)C(C)(C)C(=O)Nc1ccc(C(F)(F)F)cn1] | 2-Butylsulfamoyl-2-methyl-N-(5-trifluoromethyl-pyridin-2-yl)-propionamide |
| 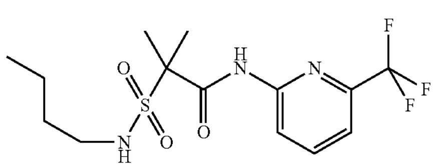 [SMILES: CCCCNS(=O)(=O)C(C)(C)C(=O)Nc1cccc(C(F)(F)F)n1] | 2-Butylsulfamoyl-2-methyl-N-(6-trifluoromethyl-pyridin-2-yl)-propionamide |

TABLE II-continued

| | |
|---|---|
| 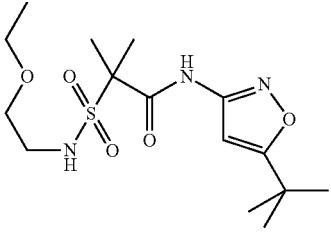 [SMILES: CCOCCNS(=O)(=O)C(C)(C)C(=O)Nc1cc(C(C)(C)C)on1] | N-(5-tert-Butyl-isoxazol-3-yl)-2-(2-ethoxy-ethylsulfamoyl)-2-methyl-propionamide |
| 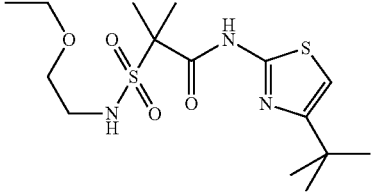 [SMILES: CCOCCNS(=O)(=O)C(C)(C)C(=O)Nc1nc(C(C)(C)C)cs1] | N-(4-tert-Butyl-thiazol-2-yl)-2-(2-ethoxy-ethylsulfamoyl)-2-methyl-propionamide |
| 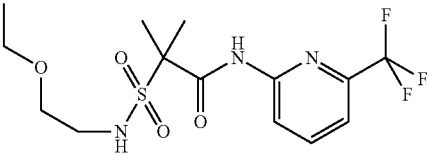 [SMILES: CCOCCNS(=O)(=O)C(C)(C)C(=O)Nc1cccc(C(F)(F)F)n1] | 2-(2-Ethoxy-ethylsulfamoyl)-2-methyl-N-(6-trifluoromethyl-pyridin-2-yl)-propionamide |
| 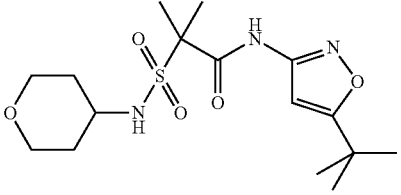 [SMILES: CC(C)(C)c1cc(NC(=O)C(C)(C)S(=O)(=O)NC2CCOCC2)no1] | N-(5-tert-Butyl-isoxazol-3-yl)-2-methyl-2-(tetrahydro-pyran-4-ylsulfamoyl)-propionamide |
| 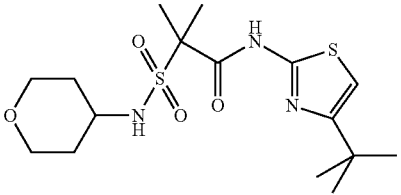 [SMILES: CC(C)(C)c1csc(NC(=O)C(C)(C)S(=O)(=O)NC2CCOCC2)n1] | N-(4-tert-Butyl-thiazol-2-yl)-2-methyl-2-(tetrahydro-pyran-4-ylsulfamoyl)-propionamide |
| 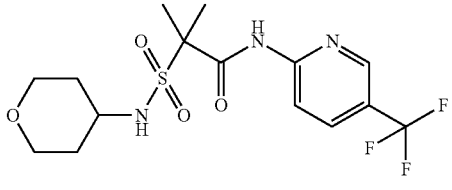 [SMILES: CC(C)(C(=O)Nc1ccc(C(F)(F)F)cn1)S(=O)(=O)NC1CCOCC1] | 2-Methyl-2-(tetrahydro-pyran-4-ylsulfamoyl)-N-(5-trifluoromethyl-pyridin-2-yl)-propionamide |
| 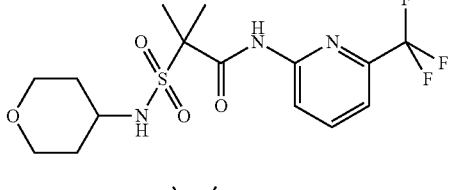 | 2-Meth-2-(tetrahydro-pyran-4-ylsulfamoyl)-N-(6-trifluoromethyl-pyridin-2-yl)-propionamide |
| 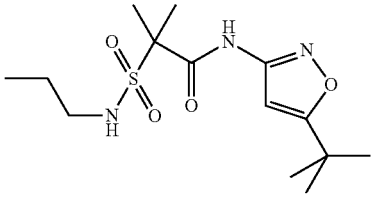 [SMILES: CCCNS(=O)(=O)C(C)(C)C(=O)Nc1cc(C(C)(C)C)on1] | N-(5-tert-Butyl-isoxazol-3-yl)-2-methyl-2-propylsulfamoyl-propionamide |

TABLE II-continued

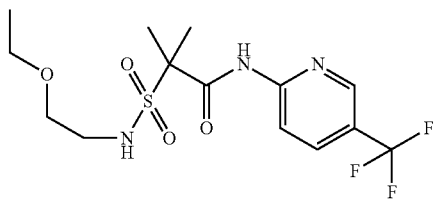 [SMILES: CCOCCNS(=O)(=O)C(C)(C)C(=O)Nc1ccc(C(F)(F)F)cn1]
2-(2-Ethoxy-ethylsulfamoyl)-2-methyl-N-(5-trifluoromethyl-pyridin-2-yl)-propionamide

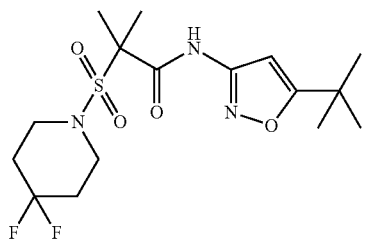 [SMILES: CC(C)(C)c1cc(NC(=O)C(C)(C)S(=O)(=O)N2CCC(F)(F)CC2)no1]
N-(5-tert-Butyl-isoxazol-3-yl)-2-(4,4-difluoro-piperidine-1-sulfonyl)-2-methyl-propionamide

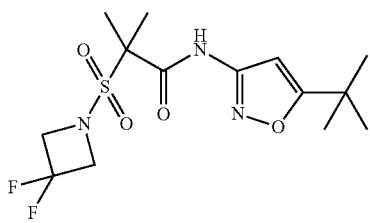 [SMILES: CC(C)(C)c1cc(NC(=O)C(C)(C)S(=O)(=O)N2CC(F)(F)C2)no1]
N-(5-tert-Butyl-isoxazol-3-yl)-2-(3,3-difluoro-azetidine-1-sulfonyl)-2-methyl-propionamide

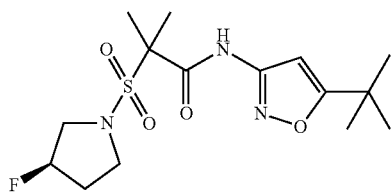 [SMILES: CC(C)(C)c1cc(NC(=O)C(C)(C)S(=O)(=O)N2CC[C@@H](F)C2)no1]
(R)-N-(5-tert-Butyl-isoxazol-3-yl)-2-(3-fluoro-pyrrolidine-1-sulfonyl)-2-methyl-propionamide

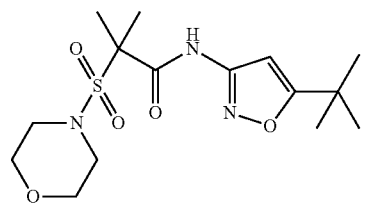 [SMILES: CC(C)(C)c1cc(NC(=O)C(C)(C)S(=O)(=O)N2CCOCC2)no1]
N-(5-tert-Butyl-isoxazol-3-yl)-2-methyl-2-(morpholine-4-sulfonyl)-propionamide

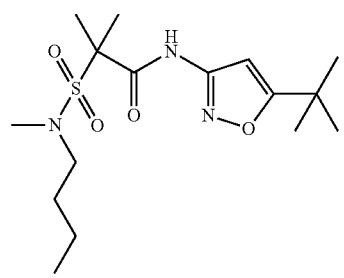 [SMILES: CCCCN(C)S(=O)(=O)C(C)(C)C(=O)Nc1cc(C(C)(C)C)on1]
N-(5-tert-Butyl-isoxazol-3-yl)-2-(butyl-methyl-sulfamoyl)-2-methyl-propionamide TABLE II-continued

| | |
|---|---|
| 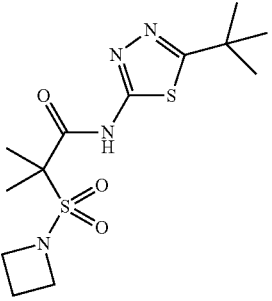 [SMILES: CC(C)(C)c1nnc(NC(=O)C(C)(C)S(=O)(=O)N2CCC2)s1] | 2-(Azetidine-1-sulfonyl)-N-(5-tert-butyl-[1,3,4]thiadiazol-2-yl)-2-methyl-propionamide |
| 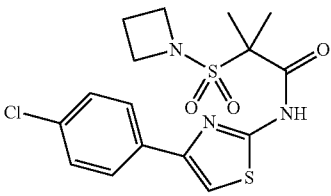 [SMILES: CC(C)(C(=O)Nc1nc(-c2ccc(Cl)cc2)cs1)S(=O)(=O)N1CCC1] | 2-(Azetidine-1-sulfonyl)-N-[4-(4-chloro-phenyl)-thiazol-2-yl]-2-methyl-propionamide |
| 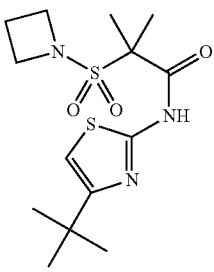 [SMILES: CC(C)(C)c1csc(NC(=O)C(C)(C)S(=O)(=O)N2CCC2)n1] | 2-(Azetidine-1-sulfonyl)-N-(4-tert-butyl-thiazol-2-yl)-2-methyl-propionamide |
| 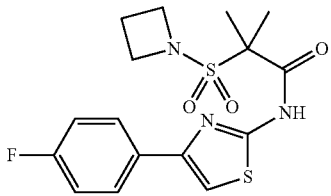 [SMILES: CC(C)(C(=O)Nc1nc(-c2ccc(F)cc2)cs1)S(=O)(=O)N1CCC1] | 2-(Azetidine-1-sulfonyl)-N-[4-(4-fluoro-phenyl)-thiazol-2-yl]-2-methyl-propionamide |
| 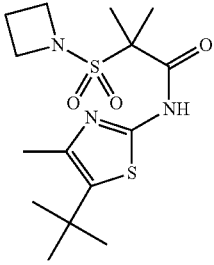 [SMILES: Cc1nc(NC(=O)C(C)(C)S(=O)(=O)N2CCC2)sc1C(C)(C)C] | 2-(Azetidine-1-sulfonyl)-N-(5-tert-butyl-4-methyl-thiazol-2-yl)-2-methyl-propionamide |
| 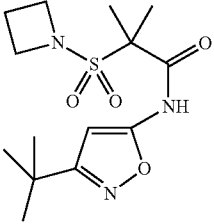 [SMILES: CC(C)(C)c1cc(NC(=O)C(C)(C)S(=O)(=O)N2CCC2)on1] | 2-(Azetidine-1-sulfonyl)-N-(3-tert-butyl-isoxazol-5-yl)-2-methyl-propionamide |

TABLE II-continued

| Structure | Name |
|---|---|
| | 2-(Azetidine-1-sulfonyl)-2-methyl-N-(3-propyl-isoxazol-5-yl)-propionamide |
| | 2-(Azetidine-1-sulfonyl)-N-[3-(2,2-dimethyl-propyl)-isoxazol-5-yl]-2-methyl-propionamide |
| | 2-(Azetidine-1-sulfonyl)-N-benzothiazol-2-yl-2-methyl-propionamide |
| | 2-(Azetidine-1-sulfonyl)-N-(4-ethyl-pyridin-2-yl)-2-methyl-propionamide |
| | 2-(Azetidine-1-sulfonyl)-2-methyl-N-(5-phenyl-[1,2,4]thiadiazol-3-yl)-propionamide |
| | 2-(Azetidine-1-sulfonyl)-2-methyl-N-(4-thiophen-2-yl-thiazol-2-yl)-propionamide |
| | 2-(Azetidine-1-sulfonyl)-N-(5-ethyl-4-phenyl-thiazol-2-yl)-2-methyl-propionamide |

TABLE II-continued

| | |
|---|---|
| 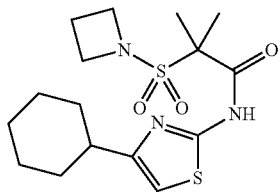 [SMILES: CC(C)(C(=O)Nc1nc(C2CCCCC2)cs1)S(=O)(=O)N1CCC1] | 2-(Azetidine-1-sulfonyl)-N-(4-cyclohexyl-thiazol-2-yl)-2-methyl-propionamide |
| 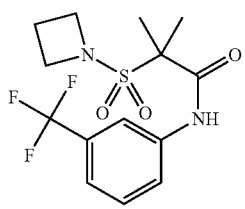 | 2-(Azetidine-1-sulfonyl)-2-methyl-N-(3-trifluoromethyl-phenyl)-propionamide |
| 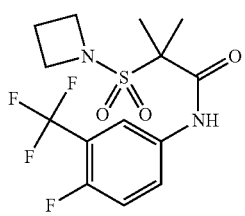 [SMILES: CC(C)(C(=O)Nc1ccc(F)c(C(F)(F)F)c1)S(=O)(=O)N1CCC1] | 2-(Azetidine-1-sulfonyl)-N-(4-fluoro-3-trifluoromethyl-phenyl)-2-methyl-propionamide |
| 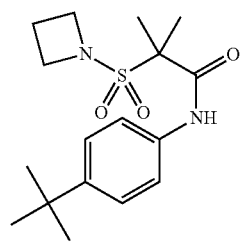 [SMILES: CC(C)(C)c1ccc(NC(=O)C(C)(C)S(=O)(=O)N2CCC2)cc1] | 2-(Azetidine-1-sulfonyl)-N-(4-tert-butyl-phenyl)-2-methyl-propionamide |
| 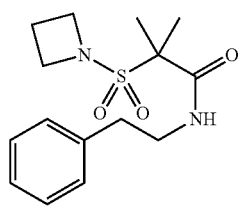 [SMILES: CC(C)(C(=O)NCCc1ccccc1)S(=O)(=O)N1CCC1] | 2-(Azetidine-1-sulfonyl)-2-methyl-N-phenethyl-propionamide |
| 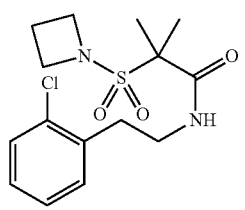 [SMILES: CC(C)(C(=O)NCCc1ccccc1Cl)S(=O)(=O)N1CCC1] | 2-(Azetidine-1-sulfonyl)-N-[2-(2-chloro-phenyl)-ethyl]-2-methyl-propionamide |
| 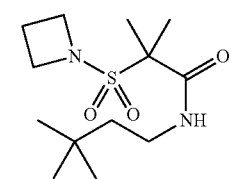 [SMILES: CC(C)(C)CCNC(=O)C(C)(C)S(=O)(=O)N1CCC1] | 2-(Azetidine-1-sulfonyl)-N-(3,3-dimethyl-butyl)-2-methyl propionamide |

TABLE II-continued

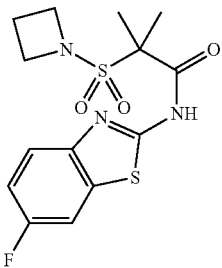
2-(Azetidine-1-sulfonyl)-N-(6-fluoro-benzothiazol-2-yl)-2-methyl-propionamide

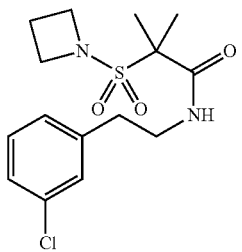 [SMILES: CC(C)(C(=O)NCCc1cccc(Cl)c1)S(=O)(=O)N1CCC1]
2-(Azetidine-1-sulfonyl)-N-[2-(3-chloro-phenyl)-ethyl]-2-methyl-propionamide

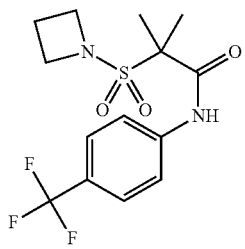 [SMILES: CC(C)(C(=O)Nc1ccc(C(F)(F)F)cc1)S(=O)(=O)N1CCC1]
2-(Azetidine-1-sulfonyl)-2-methyl-N-(4-trifluoromethyl-phenyl)-propionamide

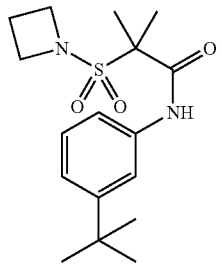 [SMILES: CC(C)(C)c1cccc(NC(=O)C(C)(C)S(=O)(=O)N2CCC2)c1]
2-(Azendine-1-sulfonyl)-N-(3-tert-butyl-phenyl)-2-methyl-propionamide

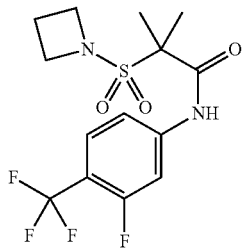 [SMILES: CC(C)(C(=O)Nc1ccc(C(F)(F)F)c(F)c1)S(=O)(=O)N1CCC1]
2-(Azetidine-1-sulfonyl)-N-(3-fluoro-4-trifluoromethyl-phenyl)-2-methyl-propionamide

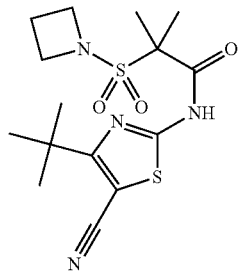 [SMILES: CC(C)(C)c1nc(NC(=O)C(C)(C)S(=O)(=O)N2CCC2)sc1C#N]
2-(Azendine-1-sulfonyl)-N-(4-tert-butyl-5-cyano-thiazol-2-yl)-2-methyl-propionamide TABLE II-continued

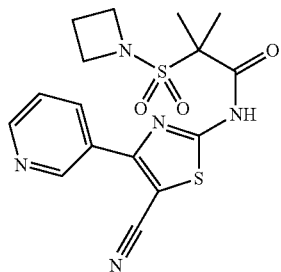 [SMILES: CC(C)(C(=O)Nc1nc(-c2cccnc2)c(C#N)s1)S(=O)(=O)N1CCC1]
2-(Azendine-1-sulfonyl)-2-methyl-N-(4-pyridin-3-yl-thiazol-2-yl)-propionarnide

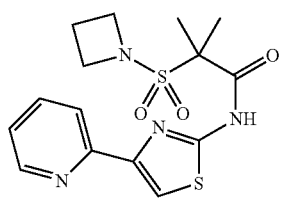
2-(Azetidine-1-sulfonyl)-2-methyl-N-(4-pyridin-2-yl-thiazol-2-yl)-propionamide

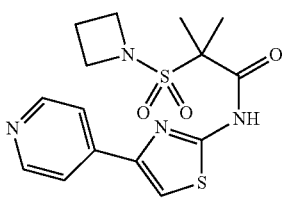
2-(Azetidine-1-sulfonyl)-2-methyl-N-(4-pyridin-4-yl-thiazol-2-yl)-propionamide

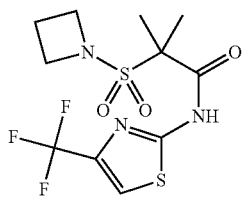 [SMILES: CC(C)(C(=O)Nc1nc(C(F)(F)F)cs1)S(=O)(=O)N1CCC1]
2-(Azetidine-1-sulfonyl)-2-methyl-N-(4-trifluorornethyl-thiazol-2-yl)-propionamide

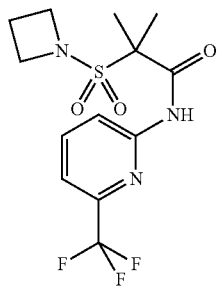 [SMILES: CC(C)(C(=O)Nc1cccc(C(F)(F)F)n1)S(=O)(=O)N1CCC1]
2-(Azetidine-1-sulfonyl)-2-rnethyl-N-(6-trifluoromethyl-pyridin-2-yl)-propionamide

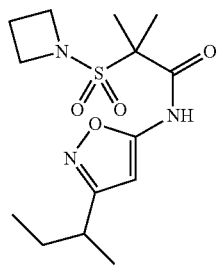 [SMILES: CCC(C)c1cc(NC(=O)C(C)(C)S(=O)(=O)N2CCC2)on1]
2-(Azetidine-1-sulfonyl)-N-(3-sec-butyl-isoxazol-5-yl)-2-methyl-propionamide TABLE II-continued

| Structure | Name |
|---|---|
| 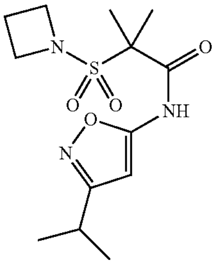 [SMILES: CC(C)c1cc(NC(=O)C(C)(C)S(=O)(=O)N2CCC2)on1] | 2-(Azetidine-1-sulfonyl)-N-(3-isopropyl-isoxazol-5-yl)-2-methyl-propionamide |
| 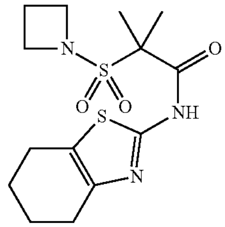 [SMILES: CC(C)(C(=O)Nc1nc2c(s1)CCCC2)S(=O)(=O)N1CCC1] | 2-(Azetidine-1-sulfonyl)-2-methyl-N-(4,5,6,7-tetrahydro-benzothiazol-2-yl)-propionamide |
| 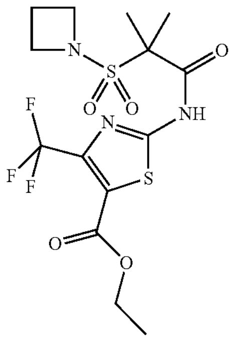 [SMILES: CCOC(=O)c1sc(NC(=O)C(C)(C)S(=O)(=O)N2CCC2)nc1C(F)(F)F] | 2-[2-(Azetidine-1-sulfonyl)-2-methyl-propionylamino]-4-trifluoromethyl-thiazole-5-carboxylic acid ethyl ester |
| 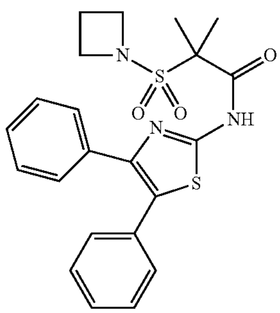 [SMILES: CC(C)(C(=O)Nc1nc(-c2ccccc2)c(-c2ccccc2)s1)S(=O)(=O)N1CCC1] | 2-(Azetidine-1-sulfonyl)-N-(4,5-diphenyl-thiazol-2-yl)-2-methyl-propionamide |
| 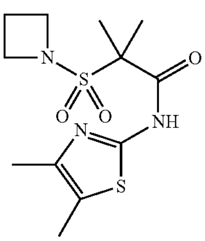 [SMILES: Cc1nc(NC(=O)C(C)(C)S(=O)(=O)N2CCC2)sc1C] | 2-(Azetidine-1-sulfonyl)-N-(4,5-dimethyl-thiazol-2-yl)-2-methyl-propionamide |
| 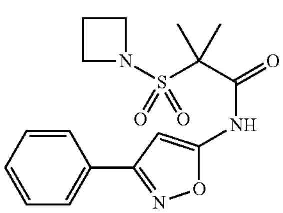 [SMILES: CC(C)(C(=O)Nc1cc(-c2ccccc2)no1)S(=O)(=O)N1CCC1] | 2-(Azetidine-1-sulfonyl)-2-methyl-N-(3-phenyl-isoxazol-5-yl)-propionamide |

TABLE II-continued

| Structure | Name |
|---|---|
| 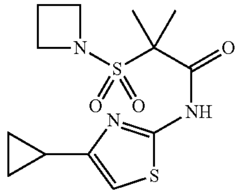 [SMILES: CC(C)(C(=O)Nc1nc(C2CC2)cs1)S(=O)(=O)N1CCC1] | 2-(Azetidine-1-sulfonyl)-N-(4-cyclopropyl-thiazol-2-yl)-2-methyl-propionamide |
| 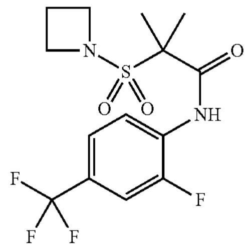 [SMILES: CC(C)(C(=O)Nc1ccc(C(F)(F)F)cc1F)S(=O)(=O)N1CCC1] | 2-(Azetidine-1-sulfonyl)-N-(2-fluoro-4-trifluoromethyl-phenyl)-2-methyl-propionamide |
| 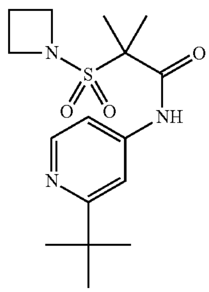 [SMILES: CC(C)(C)c1cc(NC(=O)C(C)(C)S(=O)(=O)N2CCC2)ccn1] | 2-(Azetidine-1-sulfonyl)-N-(2-tert-butyl-pyridin-4-yl)-2-methyl-propionamide |
| 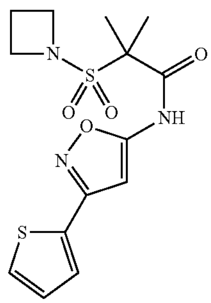 [SMILES: CC(C)(C(=O)Nc1cc(-c2cccs2)no1)S(=O)(=O)N1CCC1] | 2-(Azetidine-1-sulfonyl)-2-methyl-N-(3-thiophen-2-yl-isoxazol-5-yl)-propionamide |
| 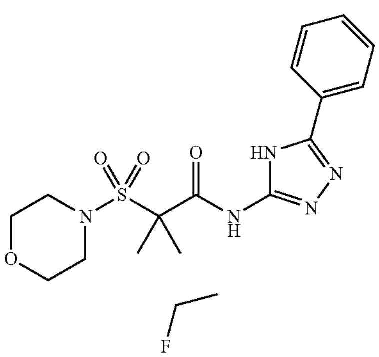 | 2-(Azetidine-1-sulfonyl)-N-[4-(4-fluoro-phenyl)-5-methyl-thiazol-2-yl]-2-methyl-propionamide |
| 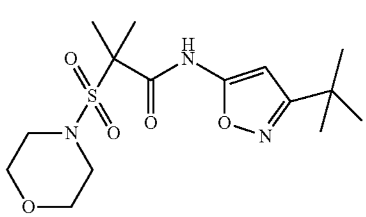 [SMILES: CC(C)(C)c1cc(NC(=O)C(C)(C)S(=O)(=O)N2CCOCC2)on1] | N(3-tert-Butyl-isoxazol-5yl)2-methyl-2-(morpholine-4-sulfonyl)-propionanide |

TABLE II-continued

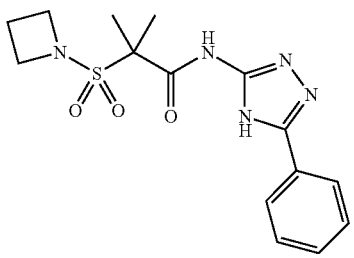 [SMILES: CC(C)(C(=O)Nc1nnc(-c2ccccc2)[nH]1)S(=O)(=O)N1CCC1]
2-(Azetidine-1-sulfonyl)-2-methyl-N-(5-phenyl-4H-[1,2,4]triazol-3-yl)-propionamide 2-Methyl-2-(morpholine-4-sulfonyl)-N-(5-phenyl-4H-[1,2,4]triazol-3-yl)-propionamide

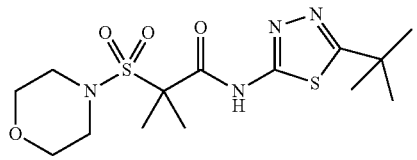 [SMILES: CC(C)(C)c1nnc(NC(=O)C(C)(C)S(=O)(=O)N2CCOCC2)s1]
N-(5-tert-Butyl-[1,3,4]thiadiazol-2-yl)-2-methyl-2-(morpholine-4-sulfonyl)-propionamide

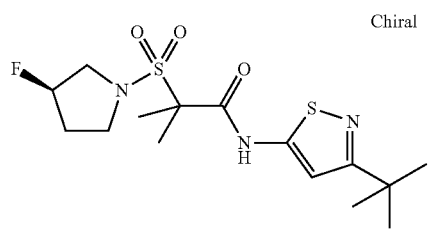 [SMILES: CC(C)(C)c1cc(NC(=O)C(C)(C)S(=O)(=O)N2CC[C@@H](F)C2)sn1]
Chiral

N-(3-tert-Butyl-isothiazol-5-yl)-2-(3-fluoro-pyrrolidine-1-sulfonyl)-2-methyl-propionamide

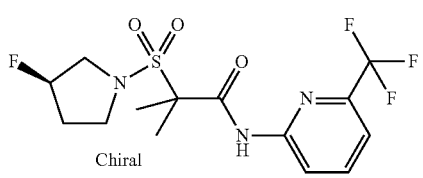 [SMILES: CC(C)(C(=O)Nc1cccc(C(F)(F)F)n1)S(=O)(=O)N1CC[C@@H](F)C1]
Chiral 2-(3-Fluoro-pyrrolidine-1-sulfonyl)-2-methyl-N-(6-trifluoromethyl-pyridin-2-yl)-propionamide

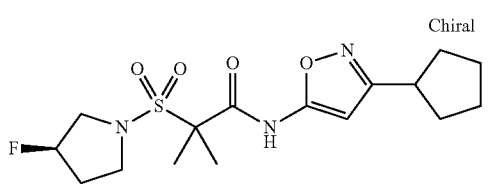 [SMILES: CC(C)(C(=O)Nc1cc(C2CCCC2)no1)S(=O)(=O)N1CC[C@@H](F)C1]
Chiral

N-(3-Cyclopentyl-isoxazol-5-yl)-2-(3(R)-fluoro-pyrrolidine-1-sulfonyl)-2-methyl-propionamide

| | 2-(3-Fluoro-pyrrolidine-1-sulfonyl)-2-methyl-N-(5-phenyl-4H-[1,2,4]triazol-3-yl)-propionamide |
| | 2-(3-Fluoro-pyrrolidine-1-sulfonyl)-2-methyl-N-(4-trifluoromethyl-thiazol-2-yl)-propionamide | or a pharmaceutically acceptable salt thereof.

Of the above compounds, the following are preferred CB2 agonists:

TABLE III

| Compound | CB2 EC50 (nM) |
| --- | --- |
| N-(5-tert-Butyl-2-methyl-2H-pyrazol-3-yl)-2-methyl-2-(morpholine-4-sulfonyl)-propionamide | 79 |
| N-(5-tert-Butyl-isoxazol-3-yl)-2-methyl-2-(2-methyl-piperidine-l-sulfony1)-propionamide | 97 |
| 2-(Azetidine-1-sulfonyl)-N-(5-tert-butyl-isoxazol-3-yl)-2-methyl-propionamide | 3.6 |
| N-(5-tert-Butyl-isoxazol-3-y1)-2-methyl-2-(pyrrolidine-1-sulfonyl)-propionamide | 1.3 |
| N-(5-tert-Butyl-isoxazol-3-yl)-2-cyclopropylsulfamoyl-2-methyl-propionamide | 58 |
| N-(5-tert-Butyl-isoxazol-3-yl)-2-cyclohexylsulfamoyl-2-methyl-propionamide | 2.4 |
| N-(5-tert-Butyl-isoxazol-3-y1)-2-methyl-2-(piperidine-1-sulfonyl)-propionamide | 6.5 |
| N-(5-tert-Butyl-isoxazol-3-yl)-2-cyclopentylsulfamoyl-2-methyl-propionamide | 13 |
| N-(5-tert-Butyl-isoxazol-3-yl)-2-butylsulfamoyl-2-methyl-propionamide | 10 |
| 2-Butylsulfamoyl-N-(4-tert-butyl-thiazol-2-yl)-2-methyl-propionamide | 32 |
| N-(5-tert-Butyl-isoxazol-3-yl)-2-methyl-2-propylsulfamoyl-propionamide | 33 |
| N-(4-tert-Butyl-thiazol-2-yl)-2-methyl-2-(methyl-phenyl-sulfamoyl)-propionamide | 42 |
| N-(5-tert-Butyl-isoxazol-3-yl)-2-(4,4-difluoro-piperidine-1-sulfonyl)-2-methyl-propionamide | 2.5 |
| N-(5-tert-Butyl-isoxazol-3-y1)-2-(3,3-difluoro-azetidine-1-sulfonyl)-2-methyl-propionamide | 5.0 |
| (R)-N-(5-tert-Butyl-isoxazol-3-y1)-2-(3-fluoro-pyrrolidine-1-sulfonyl)-2-methyl-propionamide | 5.7 |
| N-(5-tert-Butyl-isoxazol-3-yl)-2-methyl-2-(morpholine-4-sulfonyl)-propionamide | 47 |
| N-(5-tert-Butyl-isoxazol-3-yl)-2-(butyl-methyl-sulfamoyl)-2-methyl-propionamide | 1.7 |
| 2-(Azetidine-l-sulfonyl)-N-[4-(4-chloro-phenyl)-thiazol-2-yl]-2-methyl-propionamide | 8.9 |
| 2-(Azetidine-l-sulfonyl)-N-(4-tert-butyl-thiazol-2-y1)-2-methyl-propionamide | 14 |
| 2-(Azetidine-l-sulfonyl)-N-[4-(4-fluoro-phenyl)-thiazol-2-yl]-2-methyl-propionamide | 19 |
| 2-(Azetidine-l-sulfonyl)-N-(5-tert-butyl-4-methyl-thiazol-2-yl)-2-methyl-propionamide | 2.5 |
| 2-(Azetidine-l-sulfonyl)-N-(3-tert-butyl-isoxazol-5-yl)-2-methyl-propionamide | 20 |
| 2-(Azetidine-l-sulfonyl)-N-benzothiazol-2-y1-2-methyl-propionamide | 26 |
| 2-(Azetidine-l-sulfonyl)-2-methyl-N-(5-phenyl-[1,2,4]thiadiazol-3-y1)-propionamide | 72 |
| 2-(Azetidine-l-sulfonyl)-2-methyl-N-(4-thiophen-2-yl-thiazol-2-yl)-propionamide | 41 |

TABLE III-continued

| Compound | CB2 EC50 (nM) |
| --- | --- |
| 2-(Azetidine-1-sulfonyl)-N-(5-ethyl-4-phenyl-thiazol-2-yl)-2-methyl-propionamide | 6.6 |
| 2-(Azetidine-1-sulfonyl)-N-(4-cyclohexyl-thiazol-2-y1)-2-methyl-propionamide | 22 |
| 2-(Azetidine-1-sulfonyl)-N-(4-tert-butyl-phenyl)-2-methyl-propionamide | 3.1 |
| 2-(Azetidine-1-sulfonyl)-N-(3-tert-butyl-phenyl)-2-methyl-propionamide | 17 |
| 2-(Azetidine-1-sulfonyl)-N-(3-sec-butyl-isoxazol-5-y1)-2-methyl-propionamide | 14 |
| 2-(Azetidine-1-sulfonyl)-N-(3-isopropyl-isoxazol-5-y1)-2-methyl-propionamide | 108 |
| 2-(Azetidine-1-sulfonyl)-2-methyl-N-(4,5,6,7-tetrahydro-benzothiazol-2-yl)-propionamide | 62 |
| 2-(Azetidine-1-sulfonyl)-N-(2-fluoro-4-trifluoromethyl-phenyl)-2-methyl-propionamide | 86 |
| 2-(Azetidine-1-sulfonyl)-N-(2-tert-butyl-pyridin-4-y1)-2-methyl-propionamide | 37 |
| 2-(Azetidine-1-sulfonyl)-N-[4-(4-fluoro-phenyl)-5-methyl-thiazol-2-y1]-2-methyl-propionamide | 17 |
| N-(3-tert-Butyl-isoxazol-5-yl)-2-methyl-2-(morpholine-4-sulfonyl)-propionamide | 15 |
| 2-(Azetidine-1-sulfony1)-2-methyl-N-(5-phenyl-4H-[1,2,4]triazol-3-y1)-propionamide | 11 |
| 2-Methyl-2-(morpholine-4-sulfonyl)-N-(5-phenyl-4H-[1,2,4]triazol-3-y1)-propionamide | 86 |
| N-(3-tert-Butyl-isothiazol-5-y1)-2-(3-fluoro-pyrrolidine-1-sulfonyl)-2-methyl-propionamide | 83 |
| 2-(3-Fluoro-pyrrolidine-1-sulfonyl)-2-methyl-N-(5-phenyl-4H-[1,2,4]triazol-3-y1)-propionamide | 5.1 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-Dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include it's hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or poly-unsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkylthio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1$-$C_4$ alkyl)$_4^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I). In all methods, unless specified otherwise, $R^1, R^2, R^3, R^4$ and $R^5$ in the formulas below shall have the meaning of $R^1, R^2, R^3, R^4$ and $R^5$ in Formula (I) of the invention described herein above. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art.

Further modification of the initial product of formula (I) by methods known in the art and illustrated in the Examples below, may be used to prepare additional compounds of this invention.

Compounds of formula (I) may be synthesized by the method outlined in scheme 1.

Scheme 1

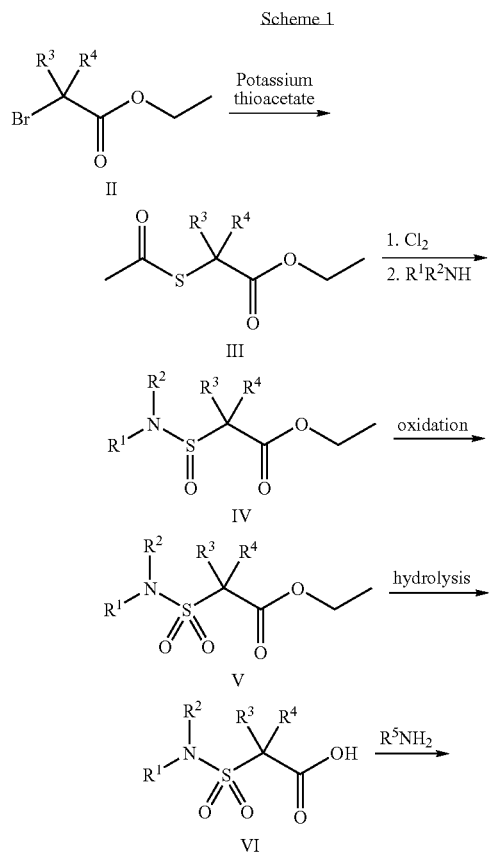

As illustrated in scheme 1, reaction of a bromo-ester of formula II with a reagent such as potassium thioacetate, in a suitable solvent, provides a sulfanyl compound of formula III. Reaction of the sulfanyl compound of formula III with chlorine affords the corresponding sulfinyl chloride. Reaction of the sulfinyl chloride with an amine $R^1R^2NH$, in a suitable solvent, provides a compound of formula IV. Oxidation of the compound of formula IV with an oxidizing agent such as meta-chloroperbenzoic acid, provides the corresponding sulfone of formula V. Hydrolysis of the sulfone V with a reagent such as potassium trimethylsilanolate, in a suitable solvent, provides the corresponding acid of formula VI.

Reaction of the acid of formula VI with thionyl chloride or oxalyl chloride affords the corresponding acid chloride which is then reacted with an amine $R^5NH_2$, in a suitable solvent, in the presence of a suitable base, to provide a compound of formula (I). Alternatively, the acid of formula VI may also be coupled with an amine $R^5NH_2$ under standard coupling conditions, to provide a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Further modification of the initial product of formula (I) by methods known in the art and illustrated in the Examples below, may be used to prepare additional compounds of this invention.

EXPERIMENTAL PROCEDURES

Method

Synthesis of N-(5-tert-butyl-isoxazol-3-yl)-2-cyclopentylsulfamoyl-2-methyl-propionamide (Example 5 in Table 4)

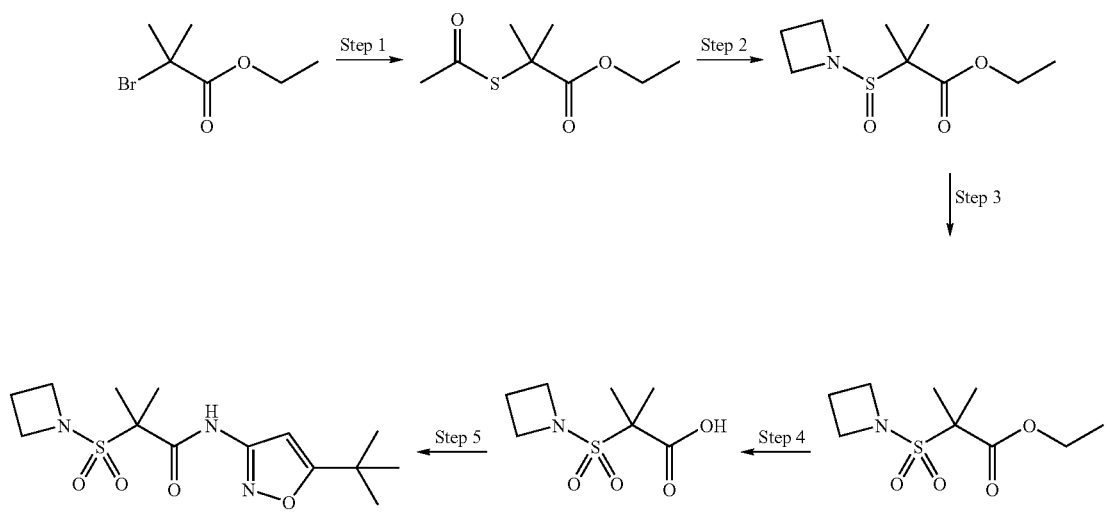

Step 1: Synthesis of 2-acetylsulfanyl-2-methyl-propionic acid ethyl ester

To a solution of ethyl α-bromoisobutyrate (62 g, 0.32 mol) in N,N-dimethylformamide (500 mL) at room temperature is added potassium thioacetate (72 g, 0.63 mol). The reaction is stirred for 16 h and then concentrated under reduced pressure. The residue is diluted with a 2M aqueous hydrochloric acid solution (500 mL) and extracted with ethyl acetate (3×500 mL). The organic fractions are combined, washed with brine (300 mL), dried (MgSO₄), filtered and concentrated under reduced pressure. Purification by chromatography on silica eluting with heptanes/dichloromethane provides the title compound, m/z 191 [M+H⁺].

Step 2: Synthesis of 2-(azetidine-1-sulfinyl)-2-methyl-propionic acid ethyl ester Chlorine gas is bubbled through a biphasic mixture of 2-acetylsulfanyl-2-methyl-propionic acid ethyl ester (5.0 g, 26 mmol) in dichloromethane (50 mL) and water (50 mL) at 10° C. for 10 min. After this time, the organic phase is separated, dried (MgSO₄), filtered and concentrated under reduced pressure. The crude sulfinyl chloride is re-dissolved in dichloromethane (50 mL) and N,N-diisopropylethylamine (4.58 mL, 26 mmol) and azetidine (1.5 g, 26 mmol) are introduced. The reaction is stirred at room temperature for 1 h and then concentrated under reduced pressure. Purification by chromatography on silica eluting with ethyl acetate/heptanes provides the title compound, m/z 220 [M+H⁺]

Using a similar procedure, the sulfinamides listed in Table IV are synthesized.

TABLE IV

| Structure | Name | m/z [M + H⁺] |
|---|---|---|
| 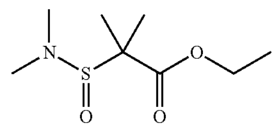 | 2-Dimethylsulfinamoyl-2-methyl-propionic acid ethyl ester | 208 |
| 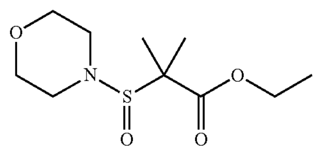 [SMILES: CCOC(=O)C(C)(C)S(=O)N1CCOCC1] | 2-Methyl-2-(morpholine-4-sulfinyl)-propionic acid ethyl ester | 250 |
| 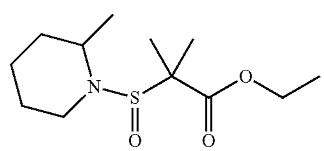 [SMILES: CCOC(=O)C(C)(C)S(=O)N1CCCCC1C] | 2-Methyl-2-(2-methyl-piperidine-1-sulfinyl)-propionic acid ethyl ester | 262 |
| 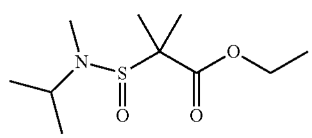 | 2-(Isopropyl-methyl-sulfinamoyl)-2-methyl-propionic acid ethyl ester | 220 |
| 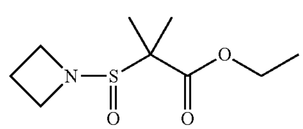 | 2-(Azetidine-1-sulfinyl)-2-methyl-propionic acid ethyl ester | 220 |
| 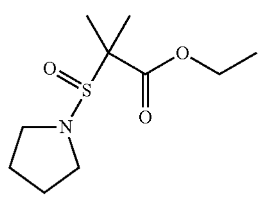 | 2-Methyl-2-(pyrrolidine-1-sulfinyl)-propionic acid ethyl ester | 234 |
| 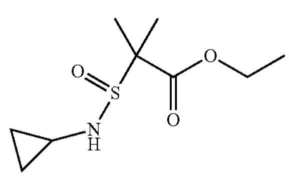 | 2-Cyclopropylsulfinamoyl-2-methyl-propionic acid ethyl ester | 220 |

TABLE IV-continued

| Structure | Name | m/z [M + H+] |
|---|---|---|
| 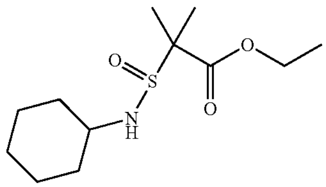 [SMILES: CCOC(=O)C(C)(C)S(=O)NC1CCCCC1] | 2-Cyclohexylsulfinamoyl-2-methyl-propionic acid ethyl ester | 262 |
| 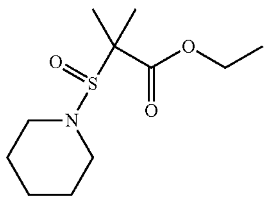 [SMILES: CCOC(=O)C(C)(C)S(=O)N1CCCCC1] | 2-Methyl-2-(piperidine-1-sulfinyl)-propionic acid ethyl ester | 248 |
| 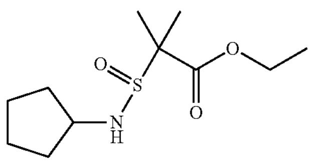 [SMILES: CCOC(=O)C(C)(C)S(=O)NC1CCCC1] | 2-Cyclopentylsulfinamoyl-2-methyl-propionic acid ethyl ester | 248 |
| 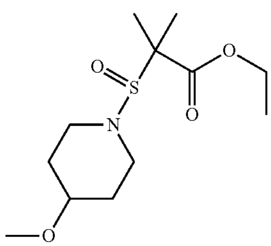 [SMILES: CCOC(=O)C(C)(C)S(=O)N1CCC(OC)CC1] | 2-(4-Methoxy-piperidine-1-sulfinyl)-2-methyl-propionic acid ethyl ester | 278 |
| 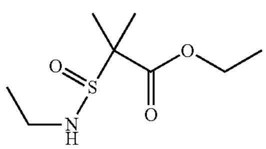 | 2-Ethylsulfinamoyl-2-methyl-propionic acid ethyl ester | 208 |
| 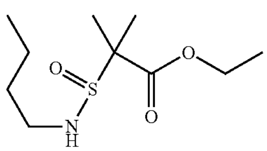 | 2-Butylsulfinamoyl-2-methyl-propionic acid ethyl ester | 236 |
| 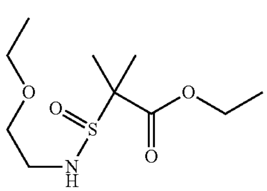 [SMILES: CCOCCNS(=O)C(C)(C)C(=O)OCC] | 2-(2-Ethoxy-ethylsulfinamoyl)-2-methyl-propionic acid ethyl ester | 252 |
| 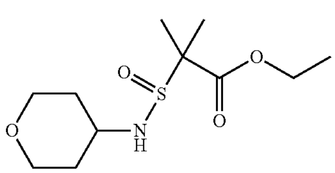 [SMILES: CCOC(=O)C(C)(C)S(=O)NC1CCOCC1] | 2-Methyl-2-(tetrahydro-pyran-4-ylsulfinamoyl)-propionic acid ethyl ester | 264 |

TABLE IV-continued

| Structure | Name | m/z [M + H⁺] |
|---|---|---|
| 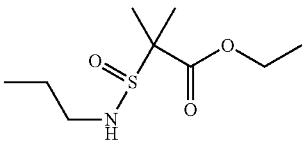 | 2-Methyl-2-propylsulfinamoyl-propionic acid ethyl ester | 222 |
| 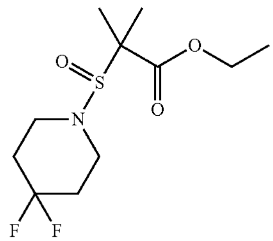 [SMILES: CCOC(=O)C(C)(C)S(=O)N1CCC(F)(F)CC1] | 2-(4,4-Difluoro-piperidine-1-sulfinyl)-2-methyl-propionic acid ethyl ester | 284 |
| 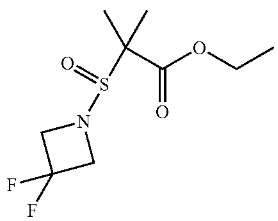 [SMILES: CCOC(=O)C(C)(C)S(=O)N1CC(F)(F)C1] | 2-(3,3-Difluoro-azetidine-1-sulfinyl)-2-methyl-propionic acid ethyl ester | 256 |
| 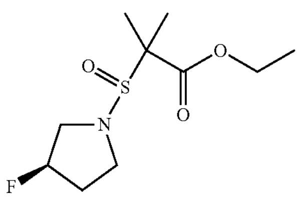 [SMILES: CCOC(=O)C(C)(C)S(=O)N1CC[C@@H](F)C1] | (R)-2-(3-Fluoro-pyrrolidine-1-sulfinyl)-2-methyl-propionic acid ethyl ester | 252 |
| 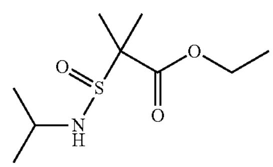 | 2-Isopropylsulfinamoyl-2-methyl-propionic acid ethyl ester | 222 |
| 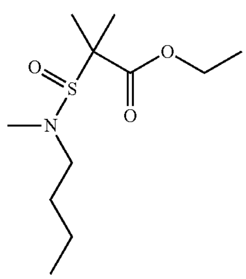 [SMILES: CCCCN(C)S(=O)C(C)(C)C(=O)OCC] | 2-(Butyl-methyl-sulfinamoyl)-2-methyl-propionic acid ethyl ester | 250 |

Step 3: Synthesis of 2-(azetidine-1-sulfonyl)-2-methyl-propionic acid ethyl ester To a solution of 2-(azetidine-1-sulfinyl)-2-methyl-propionic acid ethyl ester (4.62 g, 21 mmol) in dichloromethane (100 mL) at room temperature is added meta-chloroperbenzoic acid (5.46 g, 32 mmol). The reaction is stirred for 1 h before Ambersep 900-OH resin (2.9 g) is introduced. The suspension is shaken for 2 h and then filtered. The filtrate is concentrated under reduced pressure and the residue is re-dissolved in dichloromethane (50 mL), washed with a saturated solution of sodium bicarbonate (50 mL) and the solvent is concentrated under reduced pressure to provide the title compound as an orange oil. This oil is used without further purification, m/z 236 [M+H⁺].

Using a similar procedure, the sulfonamides listed in Table V are synthesized.

TABLE V

| Structure | Name | m/z [M + H⁺] or ¹H-NMR |
|---|---|---|
| 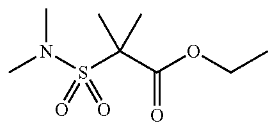 | 2-Dimethylsulfamoyl-2-methyl-propionic acid ethyl ester | 224, 241 [M + H$_2$O⁺] |
| 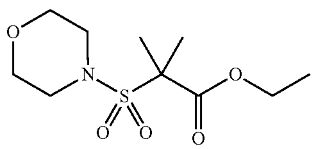 [SMILES: CCOC(=O)C(C)(C)S(=O)(=O)N1CCOCC1] | 2-Methyl-2-(morpholine-4-sulfonyl)-propionic acid ethyl ester | 266 |
| 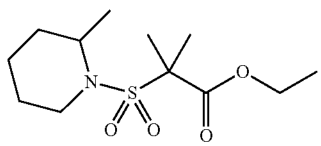 [SMILES: CCOC(=O)C(C)(C)S(=O)(=O)N1CCCCC1C] | 2-Methyl-2-(2-methyl-piperidine-1-sulfonyl)-propionic acid ethyl ester | 278 |
| 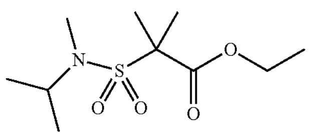 [SMILES: CCOC(=O)C(C)(C)S(=O)(=O)N(C)C(C)C] | 2-(Isopropyl-methyl-sulfamoyl)-2-methyl-propionic acid ethyl ester | 252 |
| 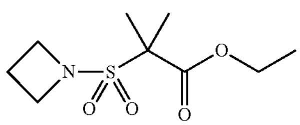 | 2-(Azetidine-1-sulfonyl)-2-methyl-propionic acid ethyl ester | 236 |
| 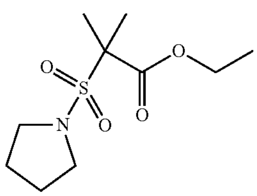 [SMILES: CCOC(=O)C(C)(C)S(=O)(=O)N1CCCC1] | 2-Methyl-2-(pyrrolidine-1-sulfonyl)-propionic acid ethyl ester | 250 |
| 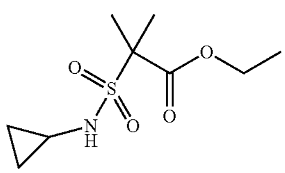 | 2-Cyclopropylsulfamoyl-2-methyl-propionic acid ethyl ester | 1H NMR (400 MHz-CHLOROFORM-d): δ ppm 0.72-0.77 (4H, m), 1.32 (3H, t, J = 7.3 Hz), 1.70 (6H, s), 2.62 (1H, m), 4.26 (2H, q, J = 7.3 Hz), 5.06 (1H, s) |
| 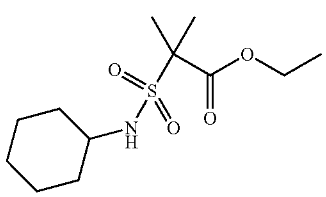 [SMILES: CCOC(=O)C(C)(C)S(=O)(=O)NC1CCCCC1] | 2-Cyclohexylsulfamoyl-2-methyl-propionic acid ethyl ester | 278 |
| 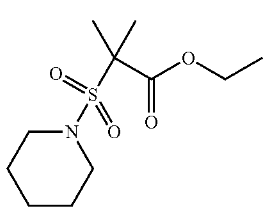 [SMILES: CCOC(=O)C(C)(C)S(=O)(=O)N1CCCCC1] | 2-Methyl-2-(piperidine-1-sulfonyl)-propionic acid ethyl ester | 264 |

TABLE V-continued

| Structure | Name | m/z [M + H+] or ¹H-NMR |
|---|---|---|
| 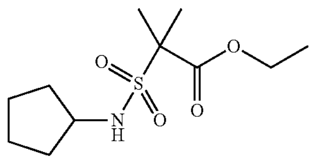 [SMILES: CCOC(=O)C(C)(C)S(=O)(=O)NC1CCCC1] | 2-Cyclopentylsulfamoyl-2-methyl-propionic acid ethyl ester | 264 |
| 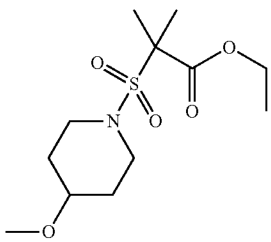 [SMILES: CCOC(=O)C(C)(C)S(=O)(=O)N1CCC(OC)CC1] | 2-(4-Methoxy-piperidine-1-sulfonyl)-2-methyl-propionic acid ethyl ester | 294 |
| 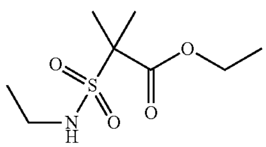 | 2-Ethylsulfamoyl-2-methyl-propionic acid ethyl ester | 224 |
| 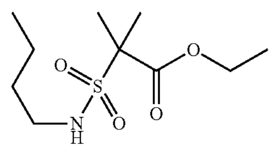 [SMILES: CCCCNS(=O)(=O)C(C)(C)C(=O)OCC] | 2-Butylsulfamoyl-2-methyl-propionic acid ethyl ester | 252 |
| 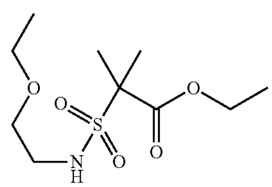 [SMILES: CCOCCNS(=O)(=O)C(C)(C)C(=O)OCC] | 2-(2-Ethoxy-ethylsulfamoyl)-2-methyl-propionic acid ethyl ester | 268 |
| 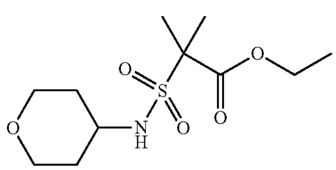 [SMILES: CCOC(=O)C(C)(C)S(=O)(=O)NC1CCOCC1] | 2-Methyl-2-(tetrahydro-pyran-4-ylsulfamoyl)-propionic acid ethyl ester | 250 |
| 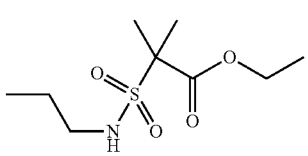 | 2-Methyl-2-propylsulfamoyl-propionic acid ethyl ester | 238 |
| 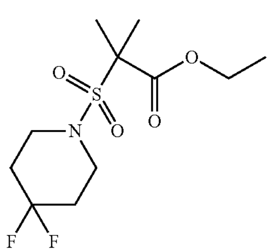 [SMILES: CCOC(=O)C(C)(C)S(=O)(=O)N1CCC(F)(F)CC1] | 2-(4,4-Difluoro-piperidine-1-sulfonyl)-2-methyl-propionic acid ethyl ester | 300 |

TABLE V-continued

| Structure | Name | m/z [M + H+] or ¹H-NMR |
|---|---|---|
| 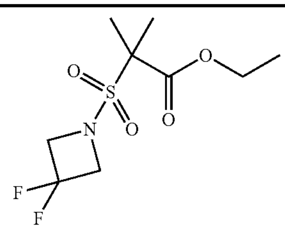 | 2-(3,3-Difluoro-azetidine-1-sulfonyl)-2-methyl-propionic acid ethyl ester | 272 |
| 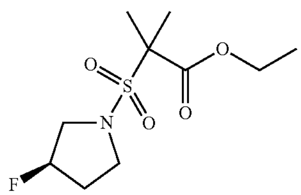 [SMILES: CCOC(=O)C(C)(C)S(=O)(=O)N1CC[C@@H](F)C1] | (R)-2-(3-Fluoro-pyrrolidine-1-sulfonyl)-2-methyl-propionic acid ethyl ester | 268 |
| 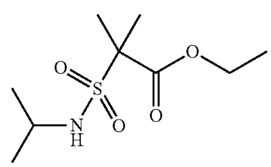 | 2-Isopropylsulfamoyl-2-methyl-propionic acid ethyl ester | 238 |
| 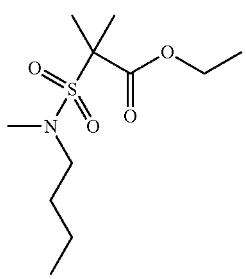 [SMILES: CCCCN(C)S(=O)(=O)C(C)(C)C(=O)OCC] | 2-(Butyl-methyl-sulfamoyl)-2-methyl-propionic acid ethyl ester | 266 |

Step 4: Synthesis of 2-(azetidine-1-sulfonyl)-2-methyl-propionic acid

To a solution of 2-(azetidine-1-sulfonyl)-2-methyl-propionic acid ethyl ester (5.0 g, 21 mmol) in tetrahydrofuran (200 mL) at room temperature is added potassium trimethylsilanolate (8.2 g, 64 mmol). The reaction is stirred for 1 h. After this time, the mixture is diluted with a solution of 1N aqueous hydrochloric acid (50 mL) and extracted with dichloromethane (250 mL). The organic phase is dried (MgSO$_4$), filtered and concentrated under reduced pressure to provide the title compound as a white solid, m/z 208 [M+H$^+$].

Using a similar procedure, the carboxylic acids listed in Table VI are synthesized.

TABLE VI

| Structure | Name | m/z [M + H+] or ¹H-NMR |
|---|---|---|
| 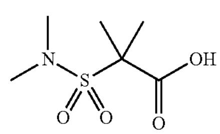 | 2-Dimethylsulfamoyl-2-methyl-propionic acid | 196, 213 [M + H$_2$O$^+$] |
| 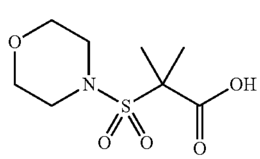 | 2-Methyl-2-(morpholine-4-sulfonyl)-propionic acid | 238 |

TABLE VI-continued

| Structure | Name | m/z [M + H⁺] or ¹H-NMR |
|---|---|---|
| 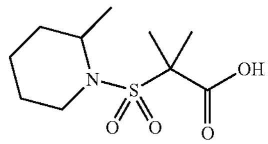 [SMILES: CC1CCCCN1S(=O)(=O)C(C)(C)C(=O)O] | 2-Methyl-2-(2-methyl-piperidine-1-sulfonyl) propionic acid | 1H NMR (400 MHz-DMSO-d6): δ ppm 1.14 (3H, d, J = 6.8 Hz), 1.40 (6H, s), 1.35-1.70 (6H, m), 2.99 (1H, dt, J = 12.2, 2.0 Hz), 3.34 (1H, m), 3.88 (1H, m) |
| 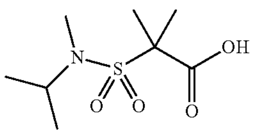 | 2-(Isopropyl-methyl-sulfamoyl)-2-methyl-propionic acid | 1H NMR (360 MHz-DMSO-d6): δ ppm 1.15 (6H, d, J = 6.6 Hz), 1.48 (6H, s), 2.72 (3H, s), 3.96 (1 H, m, J = 6.6 Hz) |
| 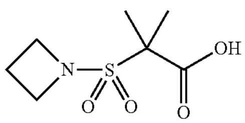 | 2-(Azetidine-1-sulfonyl)-2-methyl-propionic acid | 208 |
| 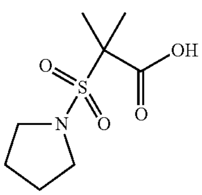 | 2-Methyl-2-(pyrrolidine-1-sulfonyl)-propionic acid | 222 |
| 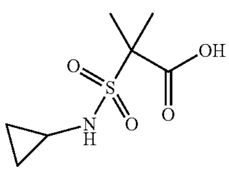 | 2-Cyclopropylsulfamoyl-2-methyl-propionic acid | 1H NMR (400 MHz-DMSO-d6): δ ppm 0.49-0.51 (4H, m), 1.45 (6H, s), 2.50 (1H, m), 7.60 (1H, br s) |
| 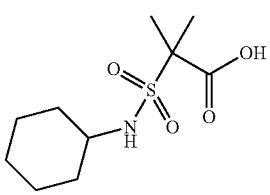 [SMILES: CC(C)(C(=O)O)S(=O)(=O)NC1CCCCC1] | 2-Cyclohexylsulfamoyl-2-methyl-propionic acid | 1H NMR (400 MHz-DMSO-d6): δ ppm 0.99 (1H, m), 1.11-1.16 (4H, m), 1.39 (6H, s), 1.42-1.47 (1H, m), 1.60 (2H, m), 1.78 (2H, m), 2.98 (1H, m), 7.10 (1H, br s) |
| 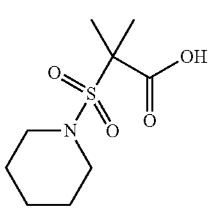 | 2-Methyl-2-(piperidine-1-sulfonyl)-propionic acid | 1H NMR (400 MHz-DMSO-d6): δ ppm 1.40 (6H, s), 1.45 (6H, m), 3.20 (4H, m) |
| 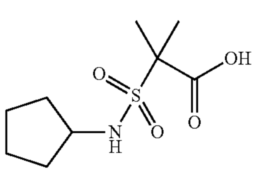 | 2-Cyclopentylsulfamoyl-2-methyl-propionic acid | 236 |

TABLE VI-continued

| Structure | Name | m/z [M + H⁺] or ¹H-NMR |
|---|---|---|
| 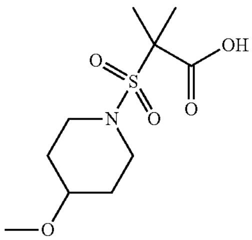 [SMILES: COC1CCN(S(=O)(=O)C(C)(C)C(=O)O)CC1] | 2-(4-Methoxy-piperidine-1-sulfonyl)-2-methyl-propionic acid | 266 |
| 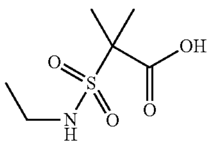 | 2-Ethylsulfamoyl-2-methyl-propionic acid | 1H NMR (400 MHz-DMSO-d6): δ ppm 1.00 (3H, t, J = 7.3 Hz), 1.40 (6H, s), 2.97 (2H, q, J = 7.3 Hz), 7.10 (1H, br s) |
| 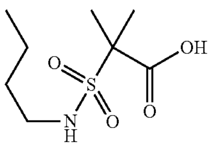 | 2-Butylsulfamoyl-2-methyl-propionic acid | 1H NMR (400 MHz-DMSO-d6): δ ppm 0.78 (3H, t, J = 7.3 Hz), 1.22 (2H, m), 1.35 (2H, m), 1.40 (6H, s), 2.93 (2H, t, J = 6.9 Hz), 7.20 (1H, br s) |
| 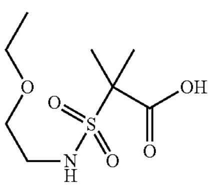 | 2-(2-Ethoxy-ethylsulfamoyl)-2-methyl-propionic acid | 1H NMR (400 MHz-DMSO-d6): δ ppm 1.04 (3H, t, J = 7.1 Hz), 1.40 (6H, s), 3.07 (2H, t, J = 6.4 Hz), 3.32 (2H, t, J = 6.4 Hz), 3.37 (2H, q, J = 7.1 Hz), 7.25 (1H, br s) |
| 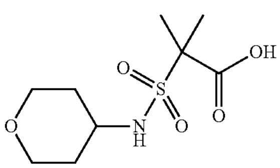 [SMILES: CC(C)(C(=O)O)S(=O)(=O)NC1CCOCC1] | 2-Methyl-2-(tetrahydro-pyran-4-ylsulfamoyl)-propionic acid | 1H NMR (400 MHz-DMSO-d6): δ ppm 1.35-1.46 (2H, m), 1.41 (6H, s), 1.67-1.74 (2H, m), 3.16-3.25 (3H, m), 3.72-3.78 (2H, m), 7.28 (1H, br s) |
| 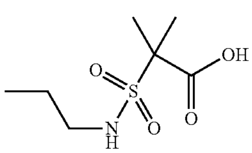 | 2-Methyl-2-propylsulfamoyl-propionic acid | 1H NMR (400 MHz-CHLOROFORM-d): δ ppm 0.97 (3H, t, J = 7.3 Hz), 1.63 (2H, m), 1.71 (6H, s), 3.23 (2H, m), 4.63 (1H, br s) |
| 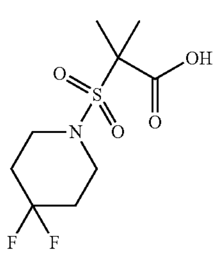 | 2-(4,4-Difluoro-piperidine-1-sulfonyl)-2-methyl-propionic acid | 1H NMR (400 MHz-DMSO-d6): δ ppm 1.43 (6H, s), 1.90-2.00 (4H, m), 3.37 (4H, m) |

TABLE VI-continued

| Structure | Name | m/z [M + H+] or 1H-NMR |
|---|---|---|
| 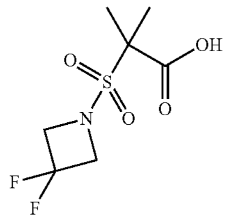 | 2-(3,3-Difluoro-azetidine-1-sulfonyl)-2-methyl-propionic acid | 1H NMR (400 MHz-CHLOROFORM-d): δ ppm 1.68 (6H, s), 4.37 (4H, t, J = 12.2 Hz) |
| 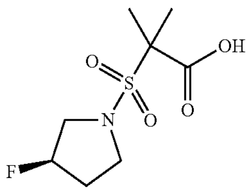 | (R)-2-(3-Fluoro-pyrrolidine-1-sulfonyl)-2-methyl-propionic acid | 1H NMR (400 MHz-CHLOROFORM-d): δ ppm 1.68 (6H, s), 1.93-2.30 (2H, m), 3.57-3.77 (4H, m), 5.18-5.31 (1H, m) |
| 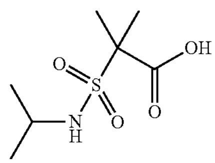 | 2-Isopropylsulfamoyl-2-methyl-propionic acid | 1H NMR (250 MHz-CHLOROFORM-d): δ ppm 1.11 (6H, d, J = 6.6 Hz), 1.52 (6H, s), 3.60 (1H, m) |
| 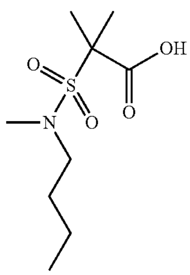 | 2-(Butyl-methyl-sulfamoyl)-2-methyl-propionic acid | 238 |

Step 5: Synthesis of 2-(azetidine-1-sulfonyl)-N-(5-tert-butyl-isoxazol-3-yl)-2-methyl-propionamide To a flask containing 2-(azetidine-1-sulfonyl)-2-methyl-propionic acid (75 mg, 0.36 mmol) is added thionyl chloride (2.5 mL). The resulting solution is heated to 60° C. where it is maintained for 2 h. After this time, the mixture is cooled to room temperature and concentrated under reduced pressure. The crude acid chloride is used without further purification.

To a solution of 3-amino-5-tert-butylisoxazole (50 mg, 0.36 mmol) in dichloromethane (1 mL) containing N,N-diisopropylethylamine (75 mL, 0.43 mmol) at room temperature is added the acid chloride (~0.36 mmol) as a solution in dichloromethane (1 mL). The reaction is stirred for 2 h and then concentrated under reduced pressure. Purification by preparative HPLC provides the title compound.

Examples listed in Table VII are prepared according to a similar procedure.

TABLE VII

Examples

| # | Structure | Name | m/z [M + H+] |
|---|---|---|---|
| 1 | 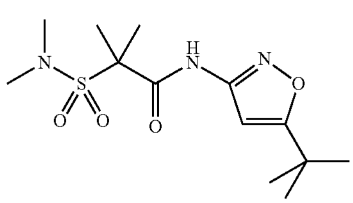 [SMILES: CN(C)S(=O)(=O)C(C)(C)C(=O)Nc1cc(C(C)(C)C)on1] | N-(5-tert-Butyl-isoxazol-3-yl)-2-dimethylsulfamoyl-2-methyl-propionamide | 340 [M + Na+], 318 |

TABLE VII-continued

Examples

| # | Structure | Name | m/z [M + H⁺] |
|---|---|---|---|
| 2 | 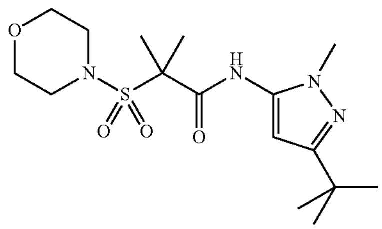 [SMILES: Cn1nc(C(C)(C)C)cc1NC(=O)C(C)(C)S(=O)(=O)N1CCOCC1] | N-(5-tert-Butyl-2-methyl-2H-pyrazol-3-yl)-2-methyl-2-(morpholine-4-sulfonyl)-propionamide | 373 |
| 3 | 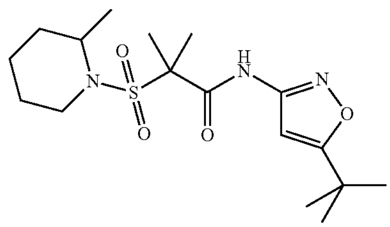 [SMILES: CC1CCCCN1S(=O)(=O)C(C)(C)C(=O)Nc1cc(C(C)(C)C)on1] | N-(5-tert-Butyl-isoxazol-3-yl)-2-methyl-2-(2-methyl-piperidine-1-sulfonyl)-propionamide | 372 |
| 4 | 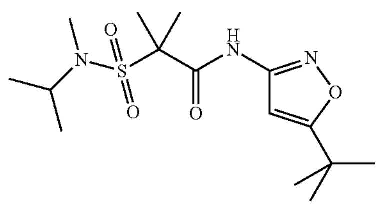 [SMILES: CC(C)N(C)S(=O)(=O)C(C)(C)C(=O)Nc1cc(C(C)(C)C)on1] | N-(5-tert-Butyl-isoxazol-3-yl)-2-(isopropyl-methyl-sulfamoyl)-2-methyl-propionamide | 346 |
| 5 | 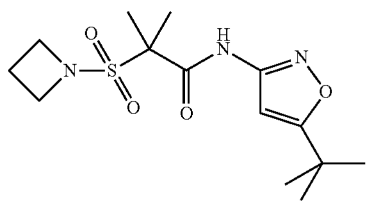 [SMILES: CC(C)(C)c1cc(NC(=O)C(C)(C)S(=O)(=O)N2CCC2)no1] | 2-(Azetidine-1-sulfonyl)-N-(5-tert-butyl-isoxazol-3-yl)-2-methyl-propionamide | 352 [M + Na⁺], 330 |
| 6 | 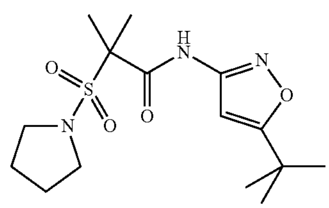 [SMILES: CC(C)(C)c1cc(NC(=O)C(C)(C)S(=O)(=O)N2CCCC2)no1] | N-(5-tert-Butyl-isoxazol-3-yl)-2-methyl-2-(pyrrolidine-1-sulfonyl)-propionamide | 366 [M + Na⁺], 344 |
| 7 | 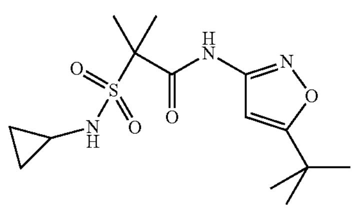 [SMILES: CC(C)(C)c1cc(NC(=O)C(C)(C)S(=O)(=O)NC2CC2)no1] | N-(5-tert-Butyl-isoxazol-3-yl)-2-cyclopropylsulfamoyl-2-methyl-propionamide | 352 [M + Na⁺], 330 |
| 8 | 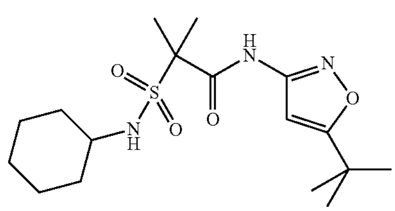 [SMILES: CC(C)(C)c1cc(NC(=O)C(C)(C)S(=O)(=O)NC2CCCCC2)no1] | N-(5-tert-Butyl-isoxazol-3-yl)-2-cyclohexylsulfamoyl-2-methyl-propionamide | 394 [M + Na⁺], 372 |

TABLE VII-continued

| # | Structure | Name | m/z [M + H+] |
|---|---|---|---|
| 9 | 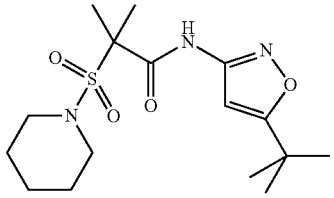 [SMILES: CC(C)(C)c1cc(NC(=O)C(C)(C)S(=O)(=O)N2CCCCC2)no1] | N-(5-tert-Butyl-isoxazol-3-yl)-2-methyl-2-(piperidine-1-sulfonyl)-propionamide | 380 [M + Na+], 358 |
| 10 | 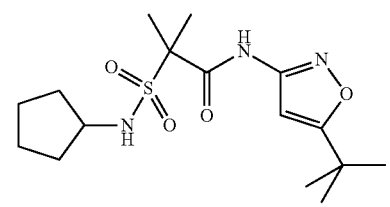 [SMILES: CC(C)(C)c1cc(NC(=O)C(C)(C)S(=O)(=O)NC2CCCC2)no1] | N-(5-tert-Butyl-isoxazol-3-yl)-2-cyclopentylsulfamoyl-2-methyl-propionamide | 358 |
| 11 | 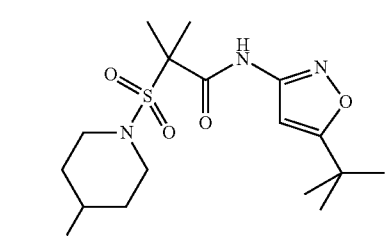 | N-(5-tert-Butyl-isoxazol-3-yl)-2-(4-methoxy-piperidine-1-sulfonyl)-2-methyl-propionamide | 410 [M + Na+], 388 |
| 12 | 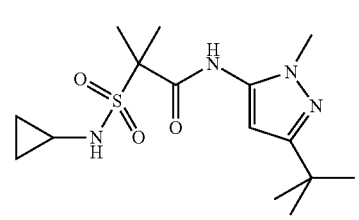 [SMILES: Cn1nc(C(C)(C)C)cc1NC(=O)C(C)(C)S(=O)(=O)NC1CC1] | N-(5-tert-Butyl-2-methyl-2H-pyrazol-3-yl)-2-cyclopropylsulfamoyl-2-methyl-propionamide | 343 |
| 13 | 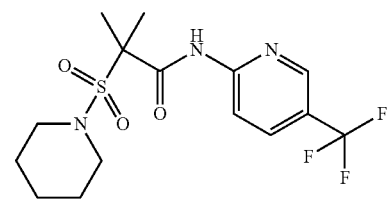 [SMILES: CC(C)(C(=O)Nc1ccc(C(F)(F)F)cn1)S(=O)(=O)N1CCCCC1] | 2-Methyl-2-(piperidine-1-sulfonyl)-N-(5-trifluoromethyl-pyridin-2-yl)-propionamide | 380 |
| 14 | 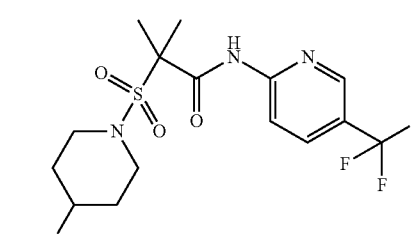 | 2-(4-Methoxy-piperidine-1-sulfonyl)-2-methyl-N-(5-trifluoromethyl-pyridin-2-yl)-propionamide | 410 |
| 15 | 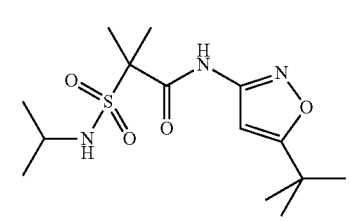 [SMILES: CC(C)NS(=O)(=O)C(C)(C)C(=O)Nc1cc(C(C)(C)C)on1] | N-(5-tert-Butyl-isoxazol-3-yl)-2-isopropylsulfamoyl-2-methyl-propionamide | 354 [M + Na+], 332 |

TABLE VII-continued

Examples

| # | Structure | Name | m/z [M + H+] |
|---|---|---|---|
| 16 | 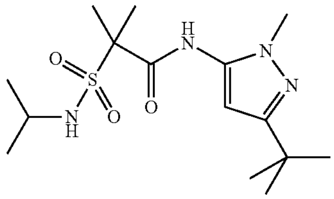 [SMILES: CC(C)NS(=O)(=O)C(C)(C)C(=O)Nc1cc(C(C)(C)C)nn1C] | N-(5-tert-Butyl-2-methyl-2H-pyrazol-3-yl)-2-isopropylsulfamoyl-2-methyl-propionamide | 345 |
| 17 | 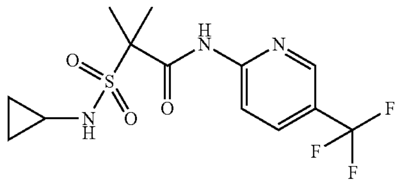 [SMILES: CC(C)(C(=O)Nc1ccc(C(F)(F)F)cn1)S(=O)(=O)NC1CC1] | 2-Cyclopropylsulfamoyl-2-methyl-N-(5-trifluoromethyl-pyridin-2-yl)-propionamide | 352 |
| 18 | 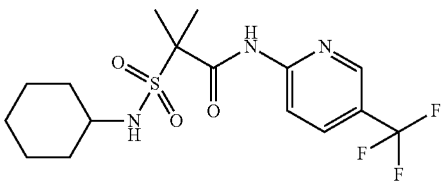 [SMILES: CC(C)(C(=O)Nc1ccc(C(F)(F)F)cn1)S(=O)(=O)NC1CCCCC1] | 2-Cyclohexylsulfamoyl-2-methyl-N-(5-trifluoromethyl-pyridin-2-yl)-propionamide | 394 |
| 19 | 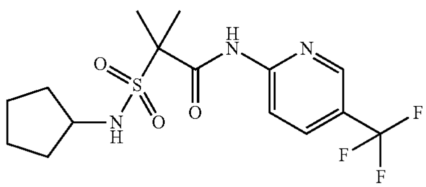 [SMILES: CC(C)(C(=O)Nc1ccc(C(F)(F)F)cn1)S(=O)(=O)NC1CCCC1] | 2-Cyclopentylsulfamoyl-2-methyl-N-(5-trifluoromethyl-pyridin-2-yl)-propionamide | 402 [M + Na+], 380 |
| 20 | 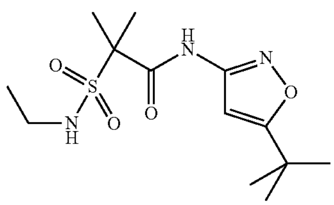 [SMILES: CCNS(=O)(=O)C(C)(C)C(=O)Nc1cc(C(C)(C)C)on1] | N-(5-tert-Butyl-isoxazol-3-yl)-2-ethylsulfamoyl-2-methyl-propionamide | 318 |
| 21 | 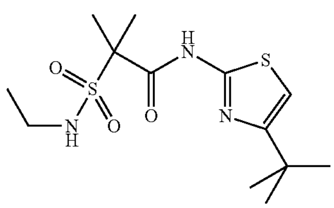 [SMILES: CCNS(=O)(=O)C(C)(C)C(=O)Nc1nc(C(C)(C)C)cs1] | N-(4-tert-Butyl-thiazol-2-yl)-2-ethylsulfamoyl-2-methyl-propionamide | 334 |
| 22 | 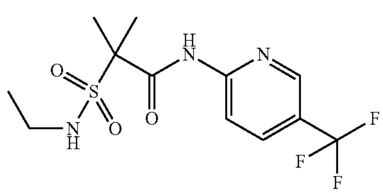 [SMILES: CCNS(=O)(=O)C(C)(C)C(=O)Nc1ccc(C(F)(F)F)cn1] | 2-Ethylsulfamoyl-2-methyl-N-(5-trifluoromethyl-pyridin-2-yl)-propionamide | 340 |
| 23 | 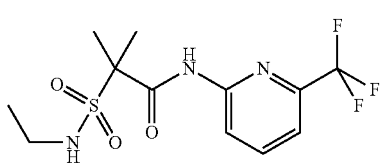 [SMILES: CCNS(=O)(=O)C(C)(C)C(=O)Nc1cccc(C(F)(F)F)n1] | 2-Ethylsulfamoyl-2-methyl-N-(6-trifluoromethyl-pyridin-2-yl)-propionamide | 362 [M + Na+], 340 |

US 8,546,563 B2

TABLE VII-continued

| # | Structure | Name | m/z [M + H⁺] |
|---|-----------|------|--------------|
| 24 | 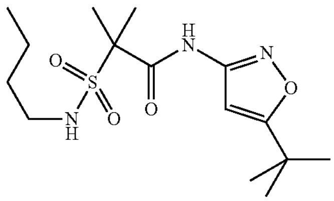 [SMILES: CCCCNS(=O)(=O)C(C)(C)C(=O)Nc1cc(C(C)(C)C)on1] | N-(5-tert-Butyl-isoxazol-3-yl)-2-butylsulfamoyl-2-methyl-propionamide | 346 |
| 25 | 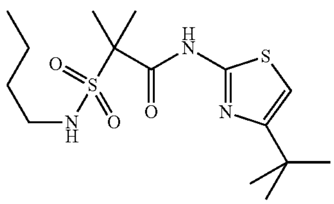 [SMILES: CCCCNS(=O)(=O)C(C)(C)C(=O)Nc1nc(C(C)(C)C)cs1] | 2-Butylsulfamoyl-N-(4-tert-butyl-thiazol-2-yl)-2-methyl-propionamide | 362 |
| 26 | 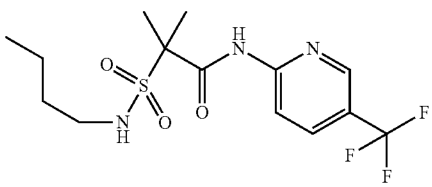 [SMILES: CCCCNS(=O)(=O)C(C)(C)C(=O)Nc1ccc(C(F)(F)F)cn1] | 2-Butylsulfamoyl-2-methyl-N-(5-trifluoromethyl-pyridin-2-yl)-propionamide | 368 |
| 27 | 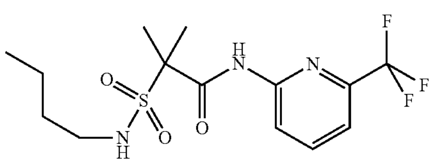 [SMILES: CCCCNS(=O)(=O)C(C)(C)C(=O)Nc1cccc(C(F)(F)F)n1] | 2-Butylsulfamoyl-2-methyl-N-(6-trifluoromethyl-pyridin-2-yl)-propionamide | 390 [M + Na⁺], 368 |
| 28 | 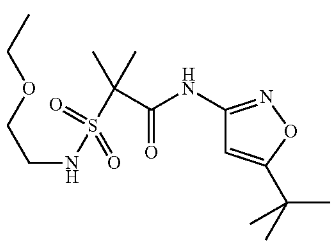 [SMILES: CCOCCNS(=O)(=O)C(C)(C)C(=O)Nc1cc(C(C)(C)C)on1] | N-(5-tert-Butyl-isoxazol-3-yl)-2-(2-ethoxy-ethylsulfamoyl)-2-methyl-propionamide | 362 |
| 29 | 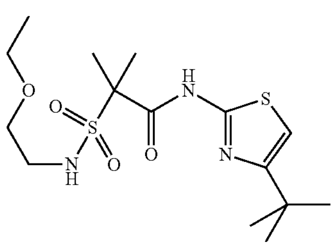 [SMILES: CCOCCNS(=O)(=O)C(C)(C)C(=O)Nc1nc(C(C)(C)C)cs1] | N-(4-tert-Butyl-thiazol-2-yl)-2-(2-ethoxy-ethylsulfamoyl)-2-methyl-propionamide | 378 |
| 30 | 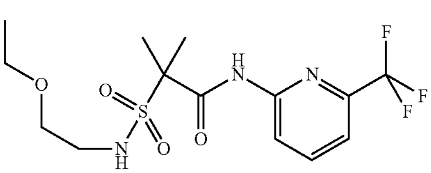 [SMILES: CCOCCNS(=O)(=O)C(C)(C)C(=O)Nc1cccc(C(F)(F)F)n1] | 2-(2-Ethoxy-ethylsulfamoyl)-2-methyl-N-(6-trifluoromethyl-pyridin-2-yl)-propionamide | 406 [M + Na⁺], 384 |

TABLE VII-continued

| # | Structure | Name | m/z [M + H+] |
|---|---|---|---|
| 31 | 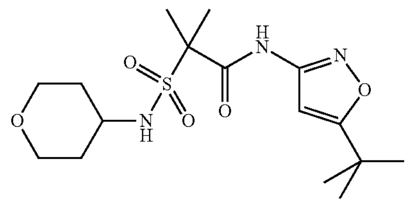 [SMILES: CC(C)(C)c1cc(NC(=O)C(C)(C)S(=O)(=O)NC2CCOCC2)no1] | N-(5-tert-Butyl-isoxazol-3-yl)-2-methyl-2-(tetrahydro-pyran-4-ylsulfamoyl)-propionamide | 374 |
| 32 | 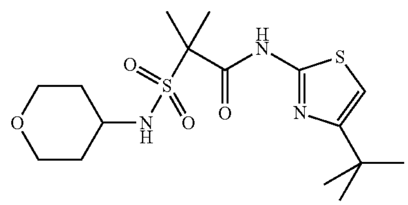 [SMILES: CC(C)(C)c1csc(NC(=O)C(C)(C)S(=O)(=O)NC2CCOCC2)n1] | N-(4-tert-Butyl-thiazol-2-yl)-2-methyl-2-(tetrahydro-pyran-4-ylsulfamoyl)-propionamide | 390 |
| 33 | 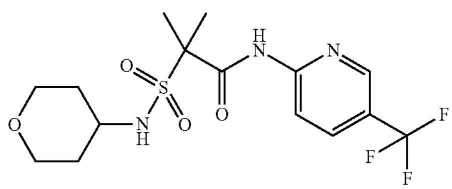 [SMILES: CC(C)(C(=O)Nc1ccc(C(F)(F)F)cn1)S(=O)(=O)NC1CCOCC1] | 2-Methyl-2-(tetrahydro-pyran-4-ylsulfamoyl)-N-(5-trifluoromethyl-pyridin-2-yl)-propionamide | 396 |
| 34 | 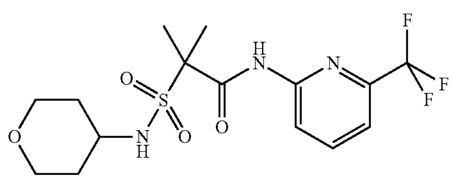 [SMILES: CC(C)(C(=O)Nc1cccc(C(F)(F)F)n1)S(=O)(=O)NC1CCOCC1] | 2-Methyl-2-(tetrahydro-pyran-4-ylsulfamoyl)-N-(6-trifluoromethyl-pyridin-2-yl)-propionamide | 418 [M + Na+], 396 |
| 35 | 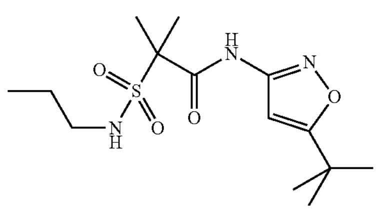 [SMILES: CCCNS(=O)(=O)C(C)(C)C(=O)Nc1cc(C(C)(C)C)on1] | N-(5-tert-Butyl-isoxazol-3-yl)-2-methyl-2-propylsulfamoyl-propionamide | 354 [M + Na+], 322 |
| 36 | 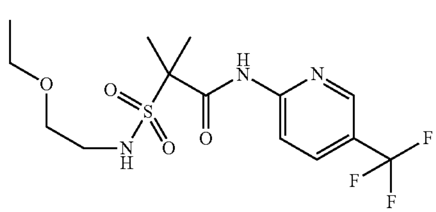 [SMILES: CCOCCNS(=O)(=O)C(C)(C)C(=O)Nc1ccc(C(F)(F)F)cn1] | 2-(2-Ethoxy-ethylsulfamoyl)-2-methyl-N-(5-trifluoromethyl-pyridin-2-yl)-propionamide | 406 [M + Na+], 384 |
| 37 | 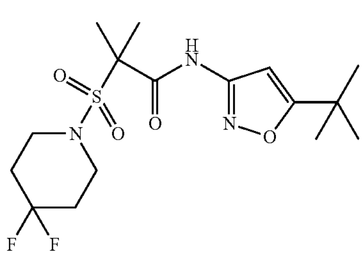 [SMILES: CC(C)(C)c1cc(NC(=O)C(C)(C)S(=O)(=O)N2CCC(F)(F)CC2)no1] | N-(5-tert-Butyl-isoxazol-3-yl)-2-(4,4-difluoro-piperidine-1-sulfonyl)-2-methyl-propionamide | 394 |

TABLE VII-continued

| # | Structure | Name | m/z [M + H+] |
|---|---|---|---|
| 38 | 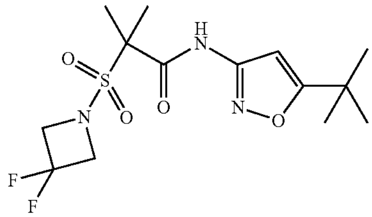 [SMILES: CC(C)(C)c1cc(NC(=O)C(C)(C)S(=O)(=O)N2CC(F)(F)C2)no1] | N-(5-tert-Butyl-isoxazol-3-yl)-2-(3,3-difluoro-azetidine-1-sulfonyl)-2-methyl-propionamide | 366 |
| 39 | 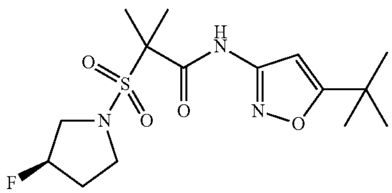 [SMILES: CC(C)(C)c1cc(NC(=O)C(C)(C)S(=O)(=O)N2CC[C@@H](F)C2)no1] | (R)-N-(5-tert-Butyl-isoxazol-3-yl)-2-(3-fluoro-pyrrolidine-1-sulfonyl)-2-methyl-propionamide | 362 |
| 40 | 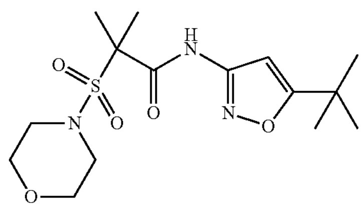 [SMILES: CC(C)(C)c1cc(NC(=O)C(C)(C)S(=O)(=O)N2CCOCC2)no1] | N-(5-tert-Butyl-isoxazol-3-yl)-2-methyl-2-morpholine-4-sulfonyl)-propionamide | 360 |
| 41 | 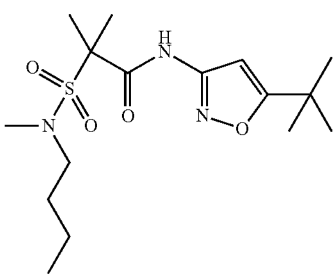 [SMILES: CCCCN(C)S(=O)(=O)C(C)(C)C(=O)Nc1cc(C(C)(C)C)on1] | N-(5-tert-Butyl-isoxazol-3-yl)-2-(butyl-methyl-sulfamoyl)-2-methyl-propionamide | 360 |
| 42 | 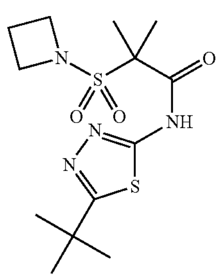 [SMILES: CC(C)(C)c1nnc(NC(=O)C(C)(C)S(=O)(=O)N2CCC2)s1] | 2-(Azetidine-1-sulfonyl)-N-(5-tert-butyl-[1,3,4]thiadiazol-2-yl)-2-methyl-propionamide | 347 |
| 43 | 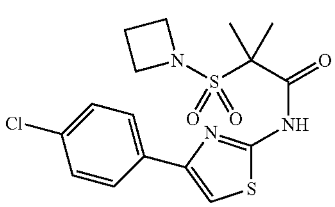 [SMILES: CC(C)(C(=O)Nc1nc(-c2ccc(Cl)cc2)cs1)S(=O)(=O)N1CCC1] | 2-(Azetidine-1-sulfonyl)-N-[4-(4-chloro-phenyl)-thiazol-2-yl]-2-methyl-propionamide | 400 |

TABLE VII-continued

| # | Structure | Name | m/z [M + H+] |
|---|---|---|---|
| 44 | 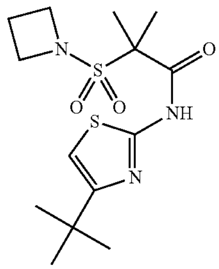 [SMILES: CC(C)(C)c1csc(NC(=O)C(C)(C)S(=O)(=O)N2CCC2)n1] | 2-(Azetidine-1-sulfonyl)-N-(4-tert-butyl-thiazol-2-yl)-2-methyl-propionamide | 346 |
| 45 | 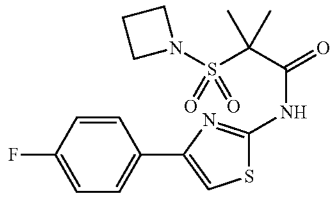 [SMILES: CC(C)(C(=O)Nc1nc(-c2ccc(F)cc2)cs1)S(=O)(=O)N1CCC1] | 2-(Azetidine-1-sulfonyl)-N-[4-(4-fluoro-phenyl)-thiazol-2-yl]-2-methyl-propionamide | 384 |
| 46 | 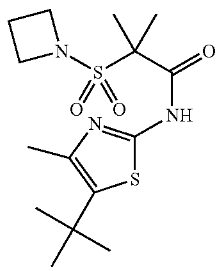 [SMILES: Cc1nc(NC(=O)C(C)(C)S(=O)(=O)N2CCC2)sc1C(C)(C)C] | 2-(Azetidine-1-sulfonyl)-N-(5-tert-butyl-4-methyl-thiazol-2-yl)-2-methyl-propionamide | 360 |
| 47 | 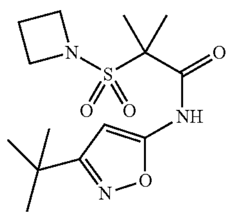 [SMILES: CC(C)(C)c1cc(NC(=O)C(C)(C)S(=O)(=O)N2CCC2)on1] | 2-(Azetidine-1-sulfonyl)-N-(3-tert-butyl-isoxazol-5-yl)-2-methyl-propionamide | 330 |
| 48 | 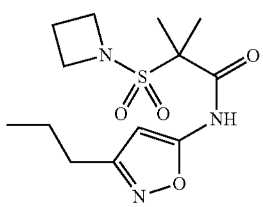 [SMILES: CCCc1cc(NC(=O)C(C)(C)S(=O)(=O)N2CCC2)on1] | 2-(Azetidine-1-sulfonyl)-2-methyl-N-(3-propyl-isoxazol-5-yl)-propionamide | 316 |
| 49 | 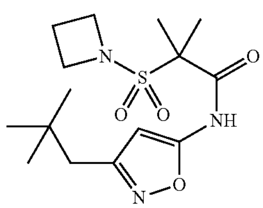 [SMILES: CC(C)(C)Cc1cc(NC(=O)C(C)(C)S(=O)(=O)N2CCC2)on1] | 2-(Azetidine-1-sulfonyl)-N-[3-(2,2-dimethyl-propyl)-isoxazol-5-yl]-2-methyl-propionamide | 344 |

TABLE VII-continued

Examples

| # | Structure | Name | m/z [M + H$^+$] |
|---|-----------|------|-----------------|
| 50 | 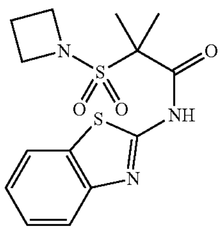 [SMILES: CC(C)(C(=O)Nc1nc2ccccc2s1)S(=O)(=O)N1CCC1] | 2-(Azetidine-1-sulfonyl)-N-benzothiazol-2-yl-2-methyl-propionamide | 340 |
| 51 | 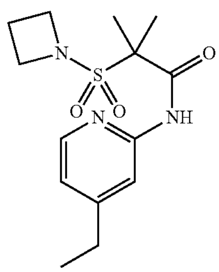 [SMILES: CCc1ccnc(NC(=O)C(C)(C)S(=O)(=O)N2CCC2)c1] | 2-(Azetidine-1-sulfonyl)-N-(4-ethyl-pyridin-2-yl)-2-methyl-propionamide | 312 |
| 52 | 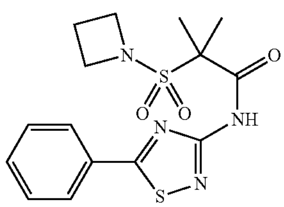 [SMILES: CC(C)(C(=O)Nc1nsc(-c2ccccc2)n1)S(=O)(=O)N1CCC1] | 2-(Azetidine-1-sulfonyl)-2-methyl-N-(5-phenyl-[1,2,4]thiadiazol-3-yl)-propionamide | 367 |
| 53 | 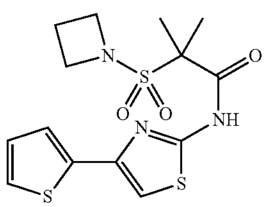 [SMILES: CC(C)(C(=O)Nc1nc(-c2cccs2)cs1)S(=O)(=O)N1CCC1] | 2-(Azetidine-1-sulfonyl)-2-methyl-N-(4-thiophen-2-yl-thiazol-2-yl)-propionamide | 372 |
| 54 | 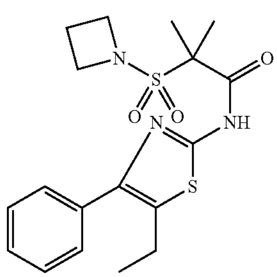 [SMILES: CCc1sc(NC(=O)C(C)(C)S(=O)(=O)N2CCC2)nc1-c1ccccc1] | 2-(Azetidine-1-sulfonyl)-N-(5-ethyl-4-phenyl-thiazol-2-yl)-2-methyl-propionamide | 384 |
| 55 | 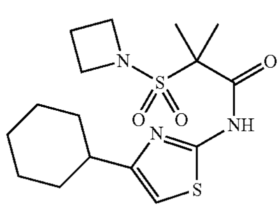 [SMILES: CC(C)(C(=O)Nc1nc(C2CCCCC2)cs1)S(=O)(=O)N1CCC1] | 2-(Azetidine-1-sulfonyl)-N-(4-cyclohexyl-thiazol-2-yl)-2-methyl-propionamide | 372 |

TABLE VII-continued

Examples

| # | Structure | Name | m/z [M + H+] |
|---|---|---|---|
| 56 | 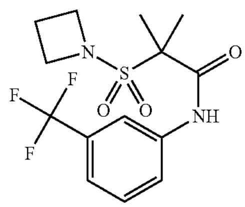 [SMILES: CC(C)(C(=O)Nc1cccc(C(F)(F)F)c1)S(=O)(=O)N1CCC1] | 2-(Azetidine-1-sulfonyl)-2-methyl-N-(3-trifluoromethyl-phenyl)-propionamide | 351 |
| 57 | 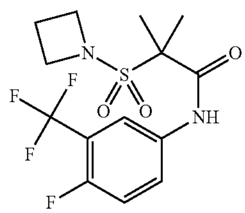 [SMILES: CC(C)(C(=O)Nc1ccc(F)c(C(F)(F)F)c1)S(=O)(=O)N1CCC1] | 2-(Azetidine-1-sulfonyl)-N-(4-fluoro-3-trifluoromethyl-phenyl)-2-methyl-propionamide | 369 |
| 58 | 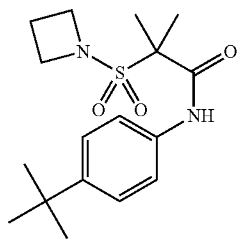 [SMILES: CC(C)(C)c1ccc(NC(=O)C(C)(C)S(=O)(=O)N2CCC2)cc1] | 2-(Azetidine-1-sulfonyl)-N-(4-tert-butyl-phenyl)-2-methyl-propionamide | 339 |
| 59 | 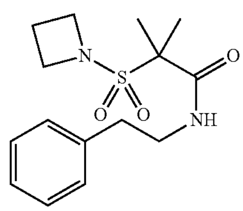 [SMILES: CC(C)(C(=O)NCCc1ccccc1)S(=O)(=O)N1CCC1] | 2-(Azetidine-1-sulfonyl)-2-methyl-N-phenethyl-propionamide | 311 |
| 60 | 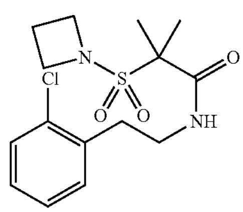 [SMILES: CC(C)(C(=O)NCCc1ccccc1Cl)S(=O)(=O)N1CCC1] | 2-(Azetidine-1-sulfonyl)-N-[2-(2-chloro-phenyl)-ethyl]-2-methyl-propionamide | 345 |
| 61 | 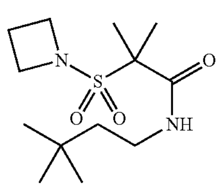 [SMILES: CC(C)(C)CCNC(=O)C(C)(C)S(=O)(=O)N1CCC1] | 2-(Azetidine-1-sulfonyl)-N-(3,3-dimethyl-butyl)-2-methyl-propionamide | 291 |
| 62 | 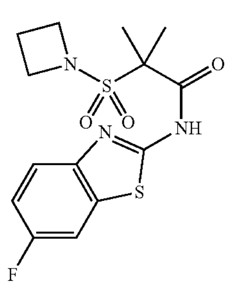 [SMILES: CC(C)(C(=O)Nc1nc2ccc(F)cc2s1)S(=O)(=O)N1CCC1] | 2-(Azetidine-1-sulfonyl)-N-(6-fluoro-benzothiazol-2-yl)-2-methyl-propionamide | 358 |

TABLE VII-continued

Examples

| # | Structure | Name | m/z [M + H$^+$] |
|---|---|---|---|
| 63 | 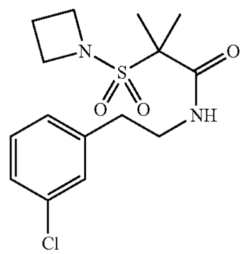 [SMILES: CC(C)(C(=O)NCCc1cccc(Cl)c1)S(=O)(=O)N1CCC1] | 2-(Azetidine-1-sulfonyl)-N-[2-(3-chloro-phenyl)-ethyl]-2-methyl-propionamide | 345 |
| 64 | 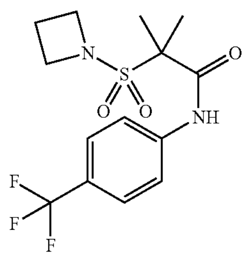 [SMILES: CC(C)(C(=O)Nc1ccc(C(F)(F)F)cc1)S(=O)(=O)N1CCC1] | 2-(Azetidine-1-sulfonyl)-2-methyl-N-(4-trifluoromethyl-phenyl)-propionamide | 351 |
| 65 | 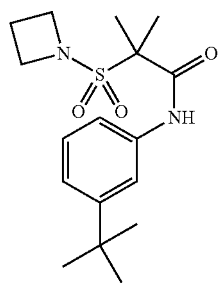 [SMILES: CC(C)(C)c1cccc(NC(=O)C(C)(C)S(=O)(=O)N2CCC2)c1] | 2-(Azetidine-1-sulfonyl)-N-(3-tert-butyl-phenyl)-2-methyl-propionamide | 339 |
| 66 | 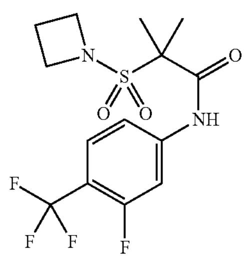 [SMILES: CC(C)(C(=O)Nc1ccc(C(F)(F)F)c(F)c1)S(=O)(=O)N1CCC1] | 2-(Azetidine-1-sulfonyl)-N-(3-fluoro-4-trifluoromethyl-phenyl)-2-methyl-propionamide | 369 |
| 67 | 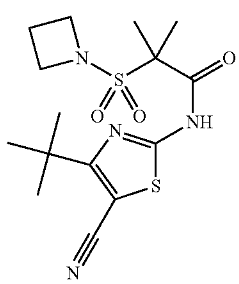 [SMILES: CC(C)(C)c1nc(NC(=O)C(C)(C)S(=O)(=O)N2CCC2)sc1C#N] | 2-(Azetidine-1-sulfonyl)-N-(4-tert-butyl-5-cyano-thiazol-2-yl)-2-methyl-propionamide | 371 |
| 68 | 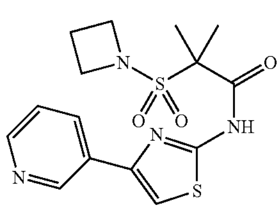 [SMILES: CC(C)(C(=O)Nc1nc(-c2cccnc2)cs1)S(=O)(=O)N1CCC1] | 2-(Azetidine-1-sulfonyl)-2-methyl-N-(4-pyridin-3-yl-thiazol-2-yl)-propionamide | 367 |

TABLE VII-continued

Examples

| # | Structure | Name | m/z [M + H+] |
|---|---|---|---|
| 69 | 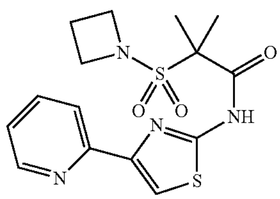 [SMILES: CC(C)(C(=O)Nc1nc(-c2ccccn2)cs1)S(=O)(=O)N1CCC1] | 2-(Azetidine-1-sulfonyl)-2-methyl-N-(4-pyridin-2-yl-thiazol-2-yl)-propionamide | 367 |
| 70 | 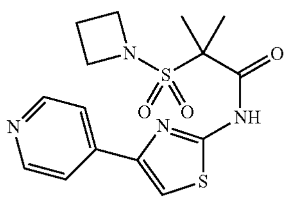 [SMILES: CC(C)(C(=O)Nc1nc(-c2ccncc2)cs1)S(=O)(=O)N1CCC1] | 2-(Azetidine-1-sulfonyl)-2-methyl-N-(4-pyridin-4-yl-thiazol-2-yl)-propionamide | 367 |
| 71 | 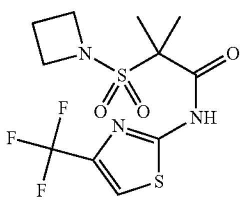 [SMILES: CC(C)(C(=O)Nc1nc(C(F)(F)F)cs1)S(=O)(=O)N1CCC1] | 2-(Azetidine-1-sulfonyl)-2-methyl-N-(4-trifluoromethyl-thiazol-2-yl)-propionamide | 358 |
| 72 | 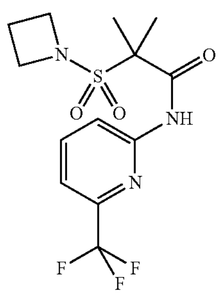 [SMILES: CC(C)(C(=O)Nc1cccc(C(F)(F)F)n1)S(=O)(=O)N1CCC1] | 2-(Azetidine-1-sulfonyl)-2-methyl-N-(6-trifluoromethyl-pyridin-2-yl)-propionamide | 352 |
| 73 | 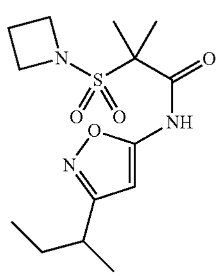 [SMILES: CCC(C)c1cc(NC(=O)C(C)(C)S(=O)(=O)N2CCC2)on1] | 2-(Azetidine-1-sulfonyl)-N-(3-sec-butyl-isoxazol-5-yl)-2-methyl-propionamide | 330 |
| 74 | 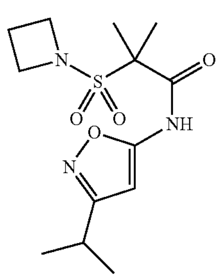 [SMILES: CC(C)c1cc(NC(=O)C(C)(C)S(=O)(=O)N2CCC2)on1] | 2-(Azetidine-1-sulfonyl)-N-(3-isopropyl-isoxazol-5-yl)-2-methyl-propionamide | 316 |

TABLE VII-continued

Examples

| # | Structure | Name | m/z [M + H⁺] |
|---|---|---|---|
| 75 | 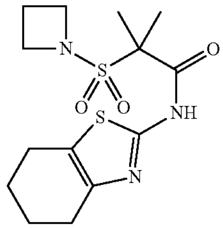 [SMILES: CC(C)(C(=O)Nc1nc2c(s1)CCCC2)S(=O)(=O)N1CCC1] | 2-(Azetidine-1-sulfonyl)-2-methyl-N-(4,5,6,7-tetrahydro-benzothiazol-2-yl)-propionamide | 344 |
| 76 | 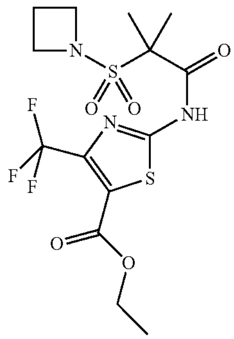 | 2-[2-(Azetidine-1-sulfonyl)-2-methyl-propionylamino]-4-trifluoromethyl-thiazole-5-carboxylic acid ethyl ester | 430 |
| 77 | 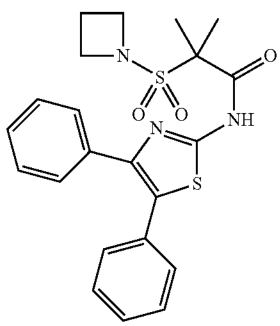 [SMILES: CC(C)(C(=O)Nc1nc(-c2ccccc2)c(-c2ccccc2)s1)S(=O)(=O)N1CCC1] | 2-(Azetidine-1-sulfonyl)-N-(4,5-diphenyl-thiazol-2-yl)-2-methyl-propionamide | 442 |
| 78 | 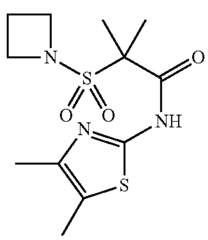 [SMILES: Cc1nc(NC(=O)C(C)(C)S(=O)(=O)N2CCC2)sc1C] | 2-(Azetidine-1-sulfonyl)-N-(4,5-dimethyl-thiazol-2-yl)-2-methyl-propionamide | 318 |
| 79 | 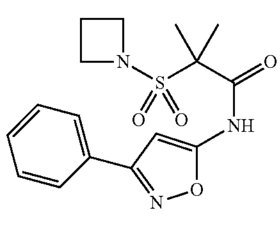 [SMILES: CC(C)(C(=O)Nc1cc(-c2ccccc2)no1)S(=O)(=O)N1CCC1] | 2-(Azetidine-1-sulfonyl)-2-methyl-N-(3-phenyl-isoxazol-5-yl)-propionamide | 350 |
| 80 | 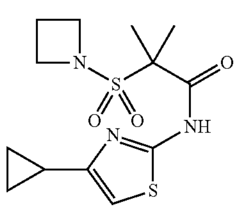 [SMILES: CC(C)(C(=O)Nc1nc(C2CC2)cs1)S(=O)(=O)N1CCC1] | 2-(Azetidine-1-sulfonyl)-N-(4-cyclopropyl-thiazol-2-yl)-2-methyl-propionamide | 330 |

TABLE VII-continued

| # | Structure | Name | m/z [M + H⁺] |
|---|---|---|---|
| 81 | 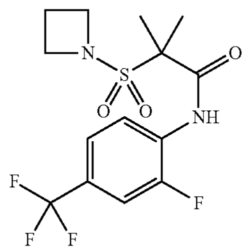 [SMILES: CC(C)(C(=O)Nc1ccc(C(F)(F)F)cc1F)S(=O)(=O)N1CCC1] | 2-(Azetidine-1-sulfonyl)-N-(2-fluoro-4-trifluoromethyl-phenyl)-2-methyl-propionamide | 369 |
| 82 | 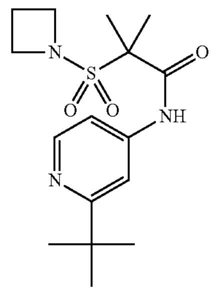 [SMILES: CC(C)(C)c1cc(NC(=O)C(C)(C)S(=O)(=O)N2CCC2)ccn1] | 2-(Azetidine-1-sulfonyl)-N-(2-tert-butyl-pyridin-4-yl)-2-methyl-propionamide | 340 |
| 83 | 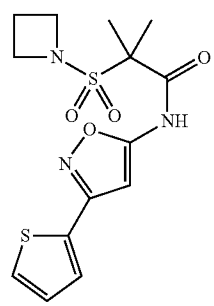 [SMILES: CC(C)(C(=O)Nc1cc(-c2cccs2)no1)S(=O)(=O)N1CCC1] | 2-(Azetidine-1-sulfonyl)-2-methyl-N-(3-thiophen-2-yl-isoxazol-5-yl)-propionamide | 356 |
| 84 | 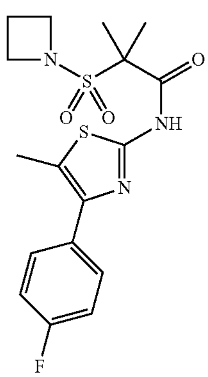 [SMILES: Cc1sc(NC(=O)C(C)(C)S(=O)(=O)N2CCC2)nc1-c1ccc(F)cc1] | 2-(Azetidine-1-sulfonyl)-N-[4-(4-fluoro-phenyl)-5-methyl-thiazol-2-yl]-2-methyl-propionamide | 398 |
| 85 | 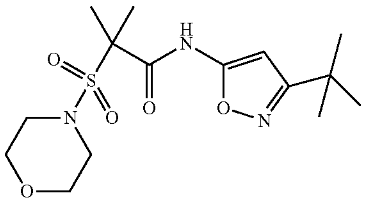 [SMILES: CC(C)(C)c1cc(NC(=O)C(C)(C)S(=O)(=O)N2CCOCC2)on1] | N-(3-tert-Butyl-isoxazol-5-yl)-2-methyl-2-(morpholine-4-sulfonyl)-propionamide | 360 |

TABLE VII-continued

Examples

| # | Structure | Name | m/z [M + H⁺] |
|---|---|---|---|
| 86 | 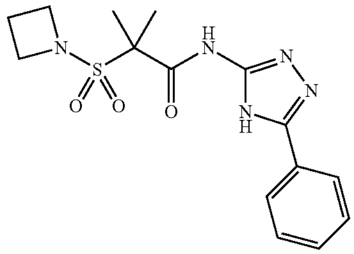 [SMILES: CC(C)(C(=O)Nc1nnc(-c2ccccc2)[nH]1)S(=O)(=O)N1CCC1] | 2-(Azetidine-1-sulfonyl)-2-methyl-N-(5-phenyl-4H-[1,2,4]triazol-3-yl)-propionamide | 350 |
| 87 | 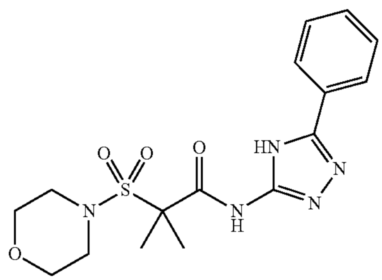 [SMILES: CC(C)(C(=O)Nc1nnc(-c2ccccc2)[nH]1)S(=O)(=O)N1CCOCC1] | 2-Methyl-2-(morpholine-4-sulfonyl)-N-(5-phenyl-4H-[1,2,4]triazol-3-yl)-propionamide | 380 |
| 88 | 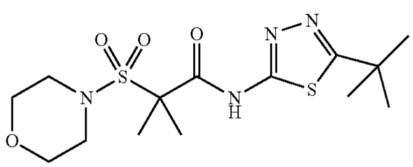 [SMILES: CC(C)(C)c1nnc(NC(=O)C(C)(C)S(=O)(=O)N2CCOCC2)s1] | N-(5-tert-Butyl-[1,3,4]thiadiazol-2-yl)-2-methyl-2-(morpholine-4-sulfonyl)-propionamide | 377 |
| 89 | Chiral | N-(3-tert-Butyl-isothiazol-5-yl)-2-(3-fluoro-pyrrolidine-1-sulfonyl)-2-methyl-propionamide | 378 |
| 90 | Chiral | 2-(3-Fluoro-pyrrolidine-1-sulfonyl)-2-methyl-N-(6-trifluoromethyl-pyridin-2-yl)-propionamide | 384 |
| 91 | Chiral | N-(3-Cyclopentyl-isoxazol-5-yl)-2-(3 (R)-fluoro-pyrrolidine-1-sulfonyl)-2-methyl-propionamide | 374 |

TABLE VII-continued

Examples

| # | Structure | Name | m/z [M + H+] |
|---|---|---|---|
| 92 | 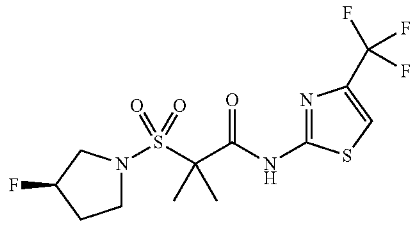 [SMILES: CC(C)(C(=O)Nc1nc(C(F)(F)F)cs1)S(=O)(=O)N1CC[C@@H](F)C1] | 2-(3-Fluoro-pyrrolidine-1-sulfonyl)-2-methyl-N-(5-phenyl-4H-[1,2,4]triazol-3-yl)-propionamide | 382 |
| 93 | 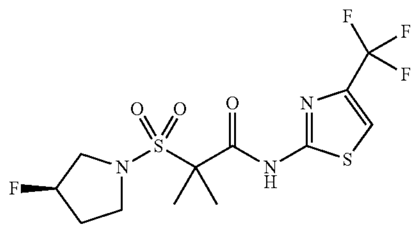 [SMILES: CC(C)(C(=O)Nc1nc(C(F)(F)F)cs1)S(=O)(=O)N1CC[C@@H](F)C1] | 2-(3-Fluoro-pyrrolidine-1-sulfonyl)-2-methyl-N-(4-trifluoromethyl-thiazol-2-yl)-propionamide | 390 |

Assessment of Biological Properties

The biological properties of the compounds of the formula I were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gα16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). IC50 values for each compound were calculated as the concentration of compound that inhibits the specific binding of the radioactively labeled ligand to the receptor by 50% using the XLFit 4.1 four parameter logistic model. IC50 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays compounds were found to exhibit agonistic activity and thus to be particularly well suited for the treatment of pain as well as for the treatment of inflammation.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine opthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.
(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;
(xxii) Cancer pain induced by or associated with tumors such as lymphatic leukemia; Hodgkin's disease, malignant lymphoma; lymphogranulomatoses; lymphosarcoma; solid malignant tumors; extensive metastases;
(xxiii) Headache such as cluster headache, migraine with and without aura, tension type headache, headache with different origins, headache disorders including prophylactic and acute use;
(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia, edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A.H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A method of treating pain comprising administering to a patient a therapeutically effective amount of a compound of the formula (I)

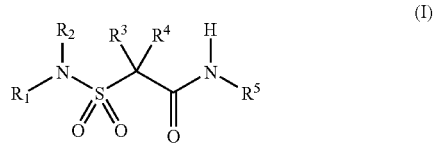

wherein, $R^1$ is $C_{1-10}$ alkyl, $C_{3-10}$ cycloalkyl-$C_{0-2}$ alkyl- or heterocycle-$C_{0-2}$ alkyl- wherein the heterocycle is chosen from tetrahydropyranyl, tetrahydrofuranyl, dioxanyl, thiomorpholinyl, 1,1-dioxo-1$\lambda^6$-thiomorpholinyl, morpholinyl, piperidinyl, pyrrolidinyl, tetrahydrothienyl, tetrahydrothiopyranyl, 1,1-dioxo-tetrahydrothiopyranyl, imidazolidinyl, pyrazolidinyl or oxetanyl, each $R^1$ is optionally substituted with 1 to 3 substituents chosen from halogen, $C_{1-5}$ alkyl, $C_{3-10}$ cycloalkyl, hydroxy or $C_{1-6}$ alkoxy;

$R^2$ is hydrogen or $C_{1-5}$ alkyl;

or $R^1$ and $R^2$ together with the N atom to which they are attached form a 3- to 6-membered heterocyclic ring optionally substituted with 1-3 substituents chosen from $C_{1-10}$ alkyl, $C_{1-10}$ alkoxy, $C_{3-10}$ cycloalkyl, hydroxyl, $C_{1-3}$ alkylaminocarbonyl, $C_{1-3}$ dialkylaminocarbonyl, $C_{1-3}$ alkylcarbonyl, $C_{1-3}$ alkyl sulfonyl or halogen;

$R^3$ is methyl, ethyl, or isopropyl;

$R^4$ is H or methyl;

or $R^3$ and $R^4$ together with the carbon they are attached to form a 3-4 membered cycloalkyl ring;

$R^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, oxadiazolyl, pyrazolyl, triazolyl, pyridinyl or benzothiazolyl each optionally independently substituted with 1 to 3 substituents chosen from $C_{1-6}$ alkyl, $C_{1-5}$ alkoxycarbonyl, cyano or halogen, each $R^5$ or it's substituents where possible are optionally partially or fully halogenated;

or a pharmaceutically acceptable salt thereof.

2. The method according to claim 1 wherein, $R^1$ is $C_{1-5}$ alkyl, $C_{3-6}$ cycloalkyl-$C_{0-2}$ alkyl- or heterocycle-$C_{0-2}$ alkyl- wherein the heterocycle is chosen from tetrahydropyranyl, tetrahydrofuranyl, dioxanyl, thiomorpholinyl, 1,1-dioxo-1$\lambda^6$-thiomorpholinyl, piperidinyl, pyrrolidinyl, tetrahydrothienyl, tetrahydrothiopyranyl, 1,1-dioxo-tetrahydrothiopyranyl, imidazolidinyl, pyrazolidinyl, oxetanyl, or morpholinyl, each $R^1$ is optionally independently substituted with 1 to 3 substituents chosen from halogen, $C_{1-5}$ alkyl, $C_{3-6}$ cycloalkyl, hydroxy or $C_{1-6}$ alkoxy;

$R^1$ and $R^2$ together with the N atom to which they are attached form morpholinyl, piperidinyl, azetidinyl, pyrrolidinyl homopiperidinyl, thiomorpholinyl, 1,1-dioxo-1$\lambda^6$-thiomorpholinyl or piperazinyl, each optionally substituted with 1-3 substituents chosen from $C_{1-3}$ alkyl, $C_{1-3}$ alkoxy, $C_{3-6}$ cycloalkyl, $C_{1-3}$ alkylaminocarbonyl, $C_{1-3}$ dialkylaminocarbonyl, $C_{1-3}$ alkylcarbonyl, $C_{1-3}$ alkyl sulfonyl or halogen;

$R^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, pyrazolyl, triazolyl, pyridinyl or benzothiazolyl each $R^5$ substituent is further optionally substituted with 1 to 3 substituents chosen from $C_{1-5}$ alkyl, $C_{1-5}$ alkoxycarbonyl, cyano or halogen, each $R^5$ or it's substituents where possible are optionally partially or fully halogenated.

3. The method according to claim 2 wherein, $R^1$ is $C_{1-5}$ alkyl, $C_{3-6}$ cycloalkyl, $C_{3-6}$ cycloalkylmethyl, tetrahydropyranyl, tetrahydrofuranyl or morpholinyl, each optionally independently substituted with 1 to 3 substituents chosen from halogen, $C_{1-3}$ alkyl, $C_{3-6}$ cycloalkyl or $C_{1-3}$ alkoxy;

$R^5$ is furanyl, pyranyl, benzoxazolyl, benzothiazolyl, benzimidazolyl, oxazolyl, imidazolyl, thienyl, pyrimidinyl, pyridazinyl, pyrazinyl, triazinyl, isoxazolyl, thiazolyl, thiadiazolyl, pyrazolyl, triazolyl, pyridinyl or benzothiazolyl each $R^5$ substituent is further optionally substituted with 1 to 3 substituents chosen from $C_{1-5}$ alkyl, $C_{1-5}$ alkoxycarbonyl, cyano or halogen, each $R^5$ or it's substituents where possible are optionally partially or fully halogenated.

4. The method according to claim 3 wherein, $R^1$ is $C_{1-5}$ alkyl, $C_{3-6}$ cycloalkyl, cyclohexylmethyl or tetrahydropyranyl, each optionally independently substituted with 1 to 3 substituents chosen from halogen, $C_{1-3}$ alkyl, $C_{3-6}$ cycloalkyl or $C_{1-4}$ alkoxy;

$R^1$ and $R^2$ together with the N atom to which they are attached form morpholinyl, piperidinyl, azetidinyl or pyrrolidinyl each optionally substituted with 1-3 substituents chosen from $C_{1-3}$ alkyl, $C_{1-3}$ alkoxy, $C_{3-6}$ cycloalkyl, $C_{1-3}$ alkylaminocarbonyl, $C_{1-3}$ dialkylaminocarbonyl, $C_{1-3}$ alkylcarbonyl, $C_{1-3}$ alkyl sulfonyl or halogen.

5. The method according to claim 4 wherein, $R^1$ is $C_{1-5}$ alkyl, $C_{3-6}$ cycloalkyl or tetrahydropyranyl, each optionally independently substituted with 1 to 3 substituents chosen from halogen, $C_{1-3}$ alkyl, $C_{1-3}$ alkoxy or $C_{3-6}$ cycloalkyl.

6. A method of treating pain comprising administering to a patient a therapeutically effective amount of a compound of the formula (I),

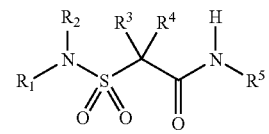

wherein for the formula (I)

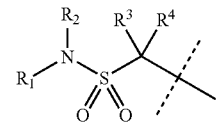

is chosen members of column A in Table I, and

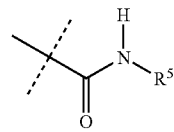

is chosen members of column B in Table I:

TABLE I

| A | B |
|---|---|
| 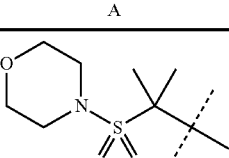 | 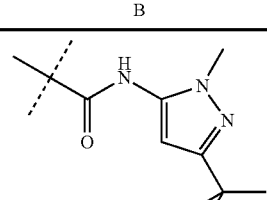 |

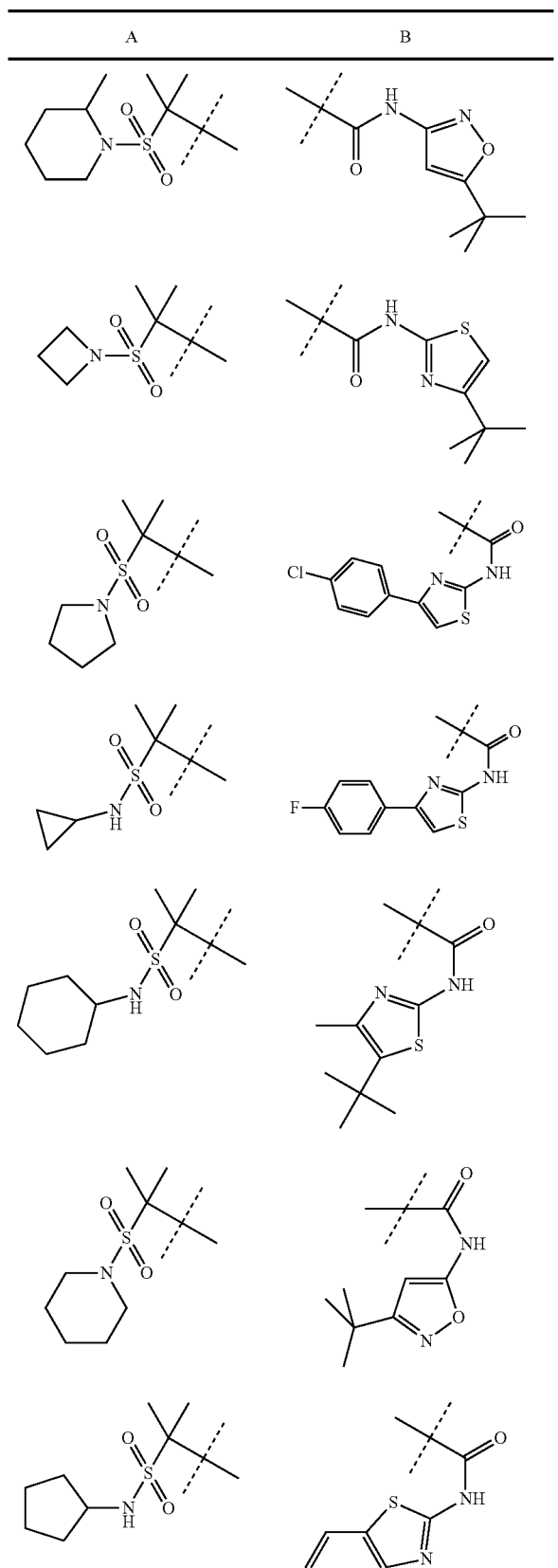

TABLE I-continued

| A | B |
|---|---|
| | (4,5,6,7-tetrahydrobenzothiazol-2-yl carboxamide structure) |
| | (2-fluoro-4-trifluoromethylphenyl carboxamide structure) |
| | (2-tert-butylpyridin-4-yl carboxamide structure) |
| | (4-(4-fluorophenyl)-5-methylthiazol-2-yl carboxamide structure) |
| | (phenyl-triazolyl ketone structure) |
| | (3-tert-butylisothiazol-5-yl carboxamide structure) |
| | (4-trifluoromethylthiazol-2-yl carboxamide structure) or |

TABLE I-continued

| A | B |
|---|---|
| | (4-cyclohexylthiazol-2-yl carboxamide structure) | or a pharmaceutically acceptable salt thereof.

7. A compound chosen from
N-(5-tert-Butyl-isoxazol-3-yl)-2-dimethylsulfamoyl-2-methyl-propionamide
N-(5-tert-Butyl-2-methyl-2H-pyrazol-3-yl)-2-methyl-2-(morpholine-4-sulfonyl)-propionamide
N-(5-tert-Butyl-isoxazol-3-yl)-2-methyl-2-(2-methyl-piperidine-1-sulfonyl)-propionamide
N-(5-tert-Butyl-isoxazol-3-yl)-2-(isopropyl-methyl-sulfamoyl)-2-methyl-propionamide
2-(Azetidine-1-sulfonyl)-N-(5-tert-butyl-isoxazol-3-yl)-2-methyl-propionamide
N-(5-tert-Butyl-isoxazol-3-yl)-2-methyl-2-(pyrrolidine-1-sulfonyl)-propionamide
N-(5-tert-Butyl-isoxazol-3-yl)-2-cyclopropylsulfamoyl-2-methyl-propionamide
N-(5-tert-Butyl-isoxazol-3-yl)-2-cyclohexylsulfamoyl-2-methyl-propionamide
N-(5-tert-Butyl-isoxazol-3-yl)-2-methyl-2-(piperidine-1-sulfonyl)-propionamide
N-(5-tert-Butyl-isoxazol-3-yl)-2-cyclopentylsulfamoyl-2-methyl-propionamide
N-(5-tert-Butyl-isoxazol-3-yl)-2-(4-methoxy-piperidine-1-sulfonyl)-2-methyl-propionamide
N-(5-tert-Butyl-2-methyl-2H-pyrazol-3-yl)-2-cyclopropylsulfamoyl-2-methyl-propionamide
2-Methyl-2-(piperidine-1-sulfonyl)-N-(5-trifluoromethyl-pyridin-2-yl)-propionamide
2-(4-Methoxy-piperidine-1-sulfonyl)-2-methyl-N-(5-trifluoromethyl-pyridin-2-yl)-propionamide
N-(5-tert-Butyl-isoxazol-3-yl)-2-isopropylsulfamoyl-2-methyl-propionamide
N-(5-tert-Butyl-2-methyl-2H-pyrazol-3-yl)-2-isopropylsulfamoyl-2-methyl-propionamide
2-Cyclopropylsulfamoyl-2-methyl-N-(5-trifluoromethyl-pyridin-2-yl)-propionamide
2-Cyclohexylsulfamoyl-2-methyl-N-(5-trifluoromethyl-pyridin-2-yl)-propionamide
2-Cyclopentylsulfamoyl-2-methyl-N-(5-trifluoromethyl-pyridin-2-yl)-propionamide
N-(5-tert-Butyl-isoxazol-3-yl)-2-ethylsulfamoyl-2-methyl-propionamide
N-(4-tert-Butyl-thiazol-2-yl)-2-ethylsulfamoyl-2-methyl-propionamide
2-Ethylsulfamoyl-2-methyl-N-(5-trifluoromethyl-pyridin-2-yl)-propionamide
2-Ethylsulfamoyl-2-methyl-N-(6-trifluoromethyl-pyridin-2-yl)-propionamide
N-(5-tert-Butyl-isoxazol-3-yl)-2-butylsulfamoyl-2-methyl-propionamide
2-Butylsulfamoyl-N-(4-tert-butyl-thiazol-2-yl)-2-methyl-propionamide 2-Butylsulfamoyl-2-methyl-N-(5-trifluoromethyl-pyridin-2-yl)-propionamide
2-Butylsulfamoyl-2-methyl-N-(6-trifluoromethyl-pyridin-2-yl)-propionamide
N-(5-tert-Butyl-isoxazol-3-yl)-2-(2-ethoxy-ethylsulfamoyl)-2-methyl-propionamide
N-(4-tert-Butyl-thiazol-2-yl)-2-(2-ethoxy-ethylsulfamoyl)-2-methyl-propionamide
2-(2-Ethoxy-ethylsulfamoyl)-2-methyl-N-(6-trifluoromethyl-pyridin-2-yl)-propionamide
N-(5-tert-Butyl-isoxazol-3-yl)-2-methyl-2-(tetrahydro-pyran-4-ylsulfamoyl)-propionamide
N-(4-tert-Butyl-thiazol-2-yl)-2-methyl-2-(tetrahydro-pyran-4-ylsulfamoyl)-propionamide
2-Methyl-2-(tetrahydro-pyran-4-ylsulfamoyl)-N-(5-trifluoromethyl-pyridin-2-yl)-propionamide
2-Methyl-2-(tetrahydro-pyran-4-ylsulfamoyl)-N-(6-trifluoromethyl-pyridin-2-yl)-propionamide
N-(5-tert-Butyl-isoxazol-3-yl)-2-methyl-2-propylsulfamoyl-propionamide
2-(2-Ethoxy-ethylsulfamoyl)-2-methyl-N-(5-trifluoromethyl-pyridin-2-yl)-propionamide
N-(5-tert-Butyl-isoxazol-3-yl)-2-(4,4-difluoro-piperidine-1-sulfonyl)-2-methyl-propionamide
N-(5-tert-Butyl-isoxazol-3-yl)-2-(3,3-difluoro-azetidine-1-sulfonyl)-2-methyl-propionamide
(R)-N-(5-tert-Butyl-isoxazol-3-yl)-2-(3-fluoro-pyrrolidine-1-sulfonyl)-2-methyl-propionamide
N-(5-tert-Butyl-isoxazol-3-yl)-2-methyl-2-(morpholine-4-sulfonyl)-propionamide
N-(5-tert-Butyl-isoxazol-3-yl)-2-(butyl-methyl-sulfamoyl)-2-methyl-propionamide
2-(Azetidine-1-sulfonyl)-N-(5-tert-butyl-[1,3,4]thiadiazol-2-yl)-2-methyl-propionamide
2-(Azetidine-1-sulfonyl)-N-[4-(4-chloro-phenyl)-thiazol-2-yl]-2-methyl-propionamide
2-(Azetidine-1-sulfonyl)-N-(4-tert-butyl-thiazol-2-yl)-2-methyl-propionamide
2-(Azetidine-1-sulfonyl)-N-[4-(4-fluoro-phenyl)-thiazol-2-yl]-2-methyl-propionamide
2-(Azetidine-1-sulfonyl)-N-(5-tert-butyl-4-methyl-thiazol-2-yl)-2-methyl-propionamide
2-(Azetidine-1-sulfonyl)-N-(3-tert-butyl-isoxazol-5-yl)-2-methyl-propionamide
2-(Azetidine-1-sulfonyl)-2-methyl-N-(3-propyl-isoxazol-5-yl)-propionamide
2-(Azetidine-1-sulfonyl)-N-[3-(2,2-dimethyl-propyl)-isoxazol-5-yl]-2-methyl-propionamide
2-(Azetidine-1-sulfonyl)-N-benzothiazol-2-yl-2-methyl-propionamide
2-(Azetidine-1-sulfonyl)-N-(4-ethyl-pyridin-2-yl)-2-methyl-propionamide
2-(Azetidine-1-sulfonyl)-2-methyl-N-(5-phenyl-[1,2,4]thiadiazol-3-yl)-propionamide
2-(Azetidine-1-sulfonyl)-2-methyl-N-(4-thiophen-2-yl-thiazol-2-yl)-propionamide
2-(Azetidine-1-sulfonyl)-N-(5-ethyl-4-phenyl-thiazol-2-yl)-2-methyl-propionamide
2-(Azetidine-1-sulfonyl)-N-(4-cyclohexyl-thiazol-2-yl)-2-methyl-propionamide
2-(Azetidine-1-sulfonyl)-2-methyl-N-(3-trifluoromethyl-phenyl)-propionamide
2-(Azetidine-1-sulfonyl)-N-(4-fluoro-3-trifluoromethyl-phenyl)-2-methyl-propionamide
2-(Azetidine-1-sulfonyl)-N-(4-tert-butyl-phenyl)-2-methyl-propionamide
2-(Azetidine-1-sulfonyl)-2-methyl-N-phenethyl-propionamide
2-(Azetidine-1-sulfonyl)-N-[2-(2-chloro-phenyl)-ethyl]-2-methyl-propionamide
2-(Azetidine-1-sulfonyl)-N-(3,3-dimethyl-butyl)-2-methyl-propionamide
2-(Azetidine-1-sulfonyl)-N-(6-fluoro-benzothiazol-2-yl)-2-methyl-propionamide
2-(Azetidine-1-sulfonyl)-N-[2-(3-chloro-phenyl)-ethyl]-2-methyl-propionamide
2-(Azetidine-1-sulfonyl)-2-methyl-N-(4-trifluoromethyl-phenyl)-propionamide
2-(Azetidine-1-sulfonyl)-N-(3-tert-butyl-phenyl)-2-methyl-propionamide
2-(Azetidine-1-sulfonyl)-N-(3-fluoro-4-trifluoromethyl-phenyl)-2-methyl-propionamide
2-(Azetidine-1-sulfonyl)-N-(4-tert-butyl-5-cyano-thiazol-2-yl)-2-methyl-propionamide
2-(Azetidine-1-sulfonyl)-2-methyl-N-(4-pyridin-3-yl-thiazol-2-yl)-propionamide
2-(Azetidine-1-sulfonyl)-2-methyl-N-(4-pyridin-2-yl-thiazol-2-yl)-propionamide
2-(Azetidine-1-sulfonyl)-2-methyl-N-(4-pyridin-4-yl-thiazol-2-yl)-propionamide
2-(Azetidine-1-sulfonyl)-2-methyl-N-(4-trifluoromethyl-thiazol-2-yl)-propionamide
2-(Azetidine-1-sulfonyl)-2-methyl-N-(6-trifluoromethyl-pyridin-2-yl)-propionamide
2-(Azetidine-1-sulfonyl)-N-(3-sec-butyl-isoxazol-5-yl)-2-methyl-propionamide
2-(Azetidine-1-sulfonyl)-N-(3-isopropyl-isoxazol-5-yl)-2-methyl-propionamide
2-(Azetidine-1-sulfonyl)-2-methyl-N-(4,5,6,7-tetrahydro-benzothiazol-2-yl)-propionamide
2-[2-(Azetidine-1-sulfonyl)-2-methyl-propionylamino]-4-trifluoromethyl-thiazole-5-carboxylic acid ethyl ester
2-(Azetidine-1-sulfonyl)-N-(4,5-diphenyl-thiazol-2-yl)-2-methyl-propionamide
2-(Azetidine-1-sulfonyl)-N-(4,5-dimethyl-thiazol-2-yl)-2-methyl-propionamide
2-(Azetidine-1-sulfonyl)-2-methyl-N-(3-phenyl-isoxazol-5-yl)-propionamide
2-(Azetidine-1-sulfonyl)-N-(4-cyclopropyl-thiazol-2-yl)-2-methyl-propionamide
2-(Azetidine-1-sulfonyl)-N-(2-fluoro-4-trifluoromethyl-phenyl)-2-methyl-propionamide
2-(Azetidine-1-sulfonyl)-N-(2-tert-butyl-pyridin-4-yl)-2-methyl-propionamide
2-(Azetidine-1-sulfonyl)-2-methyl-N-(3-thiophen-2-yl-isoxazol-5-yl)-propionamide
2-(Azetidine-1-sulfonyl)-N-[4-(4-fluoro-phenyl)-5-methyl-thiazol-2-yl]-2-methyl-propionamide
N-(3-tert-Butyl-isoxazol-5-yl)-2-methyl-2-(morpholine-4-sulfonyl)-propionamide
2-(Azetidine-1-sulfonyl)-2-methyl-N-(5-phenyl-4H-[1,2,4]triazol-3-yl)-propionamide
2-Methyl-2-(morpholine-4-sulfonyl)-N-(5-phenyl-4H-[1,2,4]triazol-3-yl)-propionamide
N-(5-tert-Butyl-[1,3,4]thiadiazol-2-yl)-2-methyl-2-(morpholine-4-sulfonyl)-propionamide
N-(3-tert-Butyl-isothiazol-5-yl)-2-(3-fluoro-pyrrolidine-1-sulfonyl)-2-methyl-propionamide
2-(3-Fluoro-pyrrolidine-1-sulfonyl)-2-methyl-N-(6-trifluoromethyl-pyridin-2-yl)-propionamide
N-(3-Cyclopentyl-isoxazol-5-yl)-2-(3(R)-fluoro-pyrrolidine-1-sulfonyl)-2-methyl-propionamide 2-(3-Fluoro-pyrrolidine-1-sulfonyl)-2-methyl-N-(5-phenyl-4H-[1,2,4]triazol-3-yl)-propionamide or
2-(3-Fluoro-pyrrolidine-1-sulfonyl)-2-methyl-N-(4-trifluoromethyl-thiazol-2-yl)-propionamide or a pharmaceutically acceptable salt thereof.

8. A compound chosen from
N-(5-tert-Butyl-2-methyl-2H-pyrazol-3-yl)-2-methyl-2-(morpholine-4-sulfonyl)-propionamide
N-(5-tert-Butyl-isoxazol-3-yl)-2-methyl-2-(2-methyl-piperidine-1-sulfonyl)-propionamide
2-(Azetidine-1-sulfonyl)-N-(5-tert-butyl-isoxazol-3-yl)-2-methyl-propionamide
N-(5-tert-Butyl-isoxazol-3-yl)-2-methyl-2-(pyrrolidine-1-sulfonyl)-propionamide
N-(5-tert-Butyl-isoxazol-3-yl)-2-cyclopropylsulfamoyl-2-methyl-propionamide
N-(5-tert-Butyl-isoxazol-3-yl)-2-cyclohexylsulfamoyl-2-methyl-propionamide
N-(5-tert-Butyl-isoxazol-3-yl)-2-methyl-2-(piperidine-1-sulfonyl)-propionamide
N-(5-tert-Butyl-isoxazol-3-yl)-2-cyclopentylsulfamoyl-2-methyl-propionamide
N-(5-tert-Butyl-isoxazol-3-yl)-2-butylsulfamoyl-2-methyl-propionamide
2-Butylsulfamoyl-N-(4-tert-butyl-thiazol-2-yl)-2-methyl-propionamide
N-(5-tert-Butyl-isoxazol-3-yl)-2-methyl-2-propylsulfamoyl-propionamide
N-(4-tert-Butyl-thiazol-2-yl)-2-methyl-2-(methyl-phenyl-sulfamoyl)-propionamide
N-(5-tert-Butyl-isoxazol-3-yl)-2-(4,4-difluoro-piperidine-1-sulfonyl)-2-methyl-propionamide
N-(5-tert-Butyl-isoxazol-3-yl)-2-(3,3-difluoro-azetidine-1-sulfonyl)-2-methyl-propionamide
(R)-N-(5-tert-Butyl-isoxazol-3-yl)-2-(3-fluoro-pyrrolidine-1-sulfonyl)-2-methyl-propionamide
N-(5-tert-Butyl-isoxazol-3-yl)-2-methyl-2-(morpholine-4-sulfonyl)-propionamide
N-(5-tert-Butyl-isoxazol-3-yl)-2-(butyl-methyl-sulfamoyl)-2-methyl-propionamide
2-(Azetidine-1-sulfonyl)-N-[4-(4-chloro-phenyl)-thiazol-2-yl]-2-methyl-propionamide
2-(Azetidine-1-sulfonyl)-N-(4-tert-butyl-thiazol-2-yl)-2-methyl-propionamide
2-(Azetidine-1-sulfonyl)-N-[4-(4-fluoro-phenyl)-thiazol-2-yl]-2-methyl-propionamide
2-(Azetidine-1-sulfonyl)-N-(5-tert-butyl-4-methyl-thiazol-2-yl)-2-methyl-propionamide
2-(Azetidine-1-sulfonyl)-N-(3-tert-butyl-isoxazol-5-yl)-2-methyl-propionamide
2-(Azetidine-1-sulfonyl)-N-benzothiazol-2-yl-2-methyl-propionamide
2-(Azetidine-1-sulfonyl)-2-methyl-N-(5-phenyl-[1,2,4]thiadiazol-3-yl)-propionamide
2-(Azetidine-1-sulfonyl)-2-methyl-N-(4-thiophen-2-yl-thiazol-2-yl)-propionamide
2-(Azetidine-1-sulfonyl)-N-(5-ethyl-4-phenyl-thiazol-2-yl)-2-methyl-propionamide
2-(Azetidine-1-sulfonyl)-N-(4-cyclohexyl-thiazol-2-yl)-2-methyl-propionamide
2-(Azetidine-1-sulfonyl)-N-(4-tert-butyl-phenyl)-2-methyl-propionamide
2-(Azetidine-1-sulfonyl)-N-(3-tert-butyl-phenyl)-2-methyl-propionamide
2-(Azetidine-1-sulfonyl)-N-(3-sec-butyl-isoxazol-5-yl)-2-methyl-propionamide
2-(Azetidine-1-sulfonyl)-N-(3-isopropyl-isoxazol-5-yl)-2-methyl-propionamide
2-(Azetidine-1-sulfonyl)-2-methyl-N-(4,5,6,7-tetrahydro-benzothiazol-2-yl)-propionamide
2-(Azetidine-1-sulfonyl)-N-(2-fluoro-4-trifluoromethyl-phenyl)-2-methyl-propionamide
2-(Azetidine-1-sulfonyl)-N-(2-tert-butyl-pyridin-4-yl)-2-methyl-propionamide
2-(Azetidine-1-sulfonyl)-N-[4-(4-fluoro-phenyl)-5-methyl-thiazol-2-yl]-2-methyl-propionamide
N-(3-tert-Butyl-isoxazol-5-yl)-2-methyl-2-(morpholine-4-sulfonyl)-propionamide
2-(Azetidine-1-sulfonyl)-2-methyl-N-(5-phenyl-4H-[1,2,4]triazol-3-yl)-propionamide
2-Methyl-2-(morpholine-4-sulfonyl)-N-(5-phenyl-4H-[1,2,4]triazol-3-yl)-propionamide
N-(3-tert-Butyl-isothiazol-5-yl)-2-(3-fluoro-pyrrolidine-1-sulfonyl)-2-methyl-propionamide or
2-(3-Fluoro-pyrrolidine-1-sulfonyl)-2-methyl-N-(5-phenyl-4H-[1,2,4]triazol-3-yl)-propionamide
or a pharmaceutically acceptable salt thereof.

9. A pharmaceutical composition comprising a therapeutically effective amount of a compound according to claim 7.

10. The method according to claim 1 wherein the pain is acute pain, visceral pain, neuropathic pain, nociceptive pain or cancer pain.

\* \* \* \* \*

UNITED STATES PATENT AND TRADEMARK OFFICE
CERTIFICATE OF CORRECTION

PATENT NO. : 8,546,563 B2
APPLICATION NO. : 12/741260
DATED : October 1, 2013
INVENTOR(S) : Berry et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 247 days.

Signed and Sealed this
Fifteenth Day of September, 2015

Michelle K. Lee
*Director of the United States Patent and Trademark Office*